(12) United States Patent
Kupershmidt et al.

(10) Patent No.: US 9,141,913 B2
(45) Date of Patent: Sep. 22, 2015

(54) CATEGORIZATION AND FILTERING OF SCIENTIFIC DATA

(75) Inventors: Ilya Kupershmidt, San Francisco, CA (US); Qiaojuan Jane Su, San Jose, CA (US); Qingdi Liu, San Jose, CA (US); Satnam Alag, Santa Clara, CA (US); Suman Sundaresh, Cupertino, CA (US)

(73) Assignee: NextBio, Santa Clara, CA (US)

( * ) Notice: Subject to any disclaimer, the term of this patent is extended or adjusted under 35 U.S.C. 154(b) by 1188 days.

(21) Appl. No.: 12/398,107

(22) Filed: Mar. 4, 2009

(65) Prior Publication Data

US 2009/0222400 A1    Sep. 3, 2009

Related U.S. Application Data

(63) Continuation-in-part of application No. 11/641,539, filed on Dec. 18, 2006, now Pat. No. 8,275,737.

(60) Provisional application No. 61/033,673, filed on Mar. 4, 2008, provisional application No. 61/089,834, filed on Aug. 18, 2008, provisional application No. 60/750,829, filed on Dec. 16, 2005.

(51) Int. Cl.
| | |
|---|---|
| G06G 7/58 | (2006.01) |
| G06N 99/00 | (2010.01) |
| G06F 19/22 | (2011.01) |
| G01N 33/48 | (2006.01) |
| G06F 19/18 | (2011.01) |

(52) U.S. Cl.
CPC .............. *G06N 99/005* (2013.01); *G06F 19/22* (2013.01); *G06F 19/18* (2013.01)

(58) Field of Classification Search
CPC ................................. G06F 19/18; G06F 19/22
See application file for complete search history.

(56) References Cited

U.S. PATENT DOCUMENTS

| | | | |
|---|---|---|---|
| 5,153,178 A | 10/1992 | Maroko | |
| 6,151,601 A | 11/2000 | Papierniak et al. | |
| 6,286,002 B1 | 9/2001 | Axaopoulos et al. | |
| 6,408,308 B1 | 6/2002 | Maslyn et al. | |
| 6,465,183 B2 | 10/2002 | Wolber | |
| 6,925,455 B2 | 8/2005 | Gong et al. | |
| 6,947,846 B2 | 9/2005 | Quake et al. | |
| 7,072,665 B1 | 7/2006 | Blumberg et al. | |
| 7,103,519 B2 | 9/2006 | Singarajan et al. | |
| 7,155,453 B2 | 12/2006 | Kincaid | |
| 7,225,183 B2 | 5/2007 | Gardner | |
| 7,243,112 B2 | 7/2007 | Qu et al. | |
| 7,761,392 B2 | 7/2010 | Mohamed et al. | |
| 7,798,401 B2 | 9/2010 | Jung et al. | |
| 7,930,172 B2 | 4/2011 | Bellegarda | |
| 8,078,217 B2 | 12/2011 | Garcia | |
| 8,275,737 B2 | 9/2012 | Kupershmidt et al. | |
| 8,364,665 B2 | 1/2013 | Su et al. | |
| 2001/0005852 A1 | 6/2001 | Bogle et al. | |
| 2001/0016314 A1 | 8/2001 | Anderson et al. | |
| 2002/0093591 A1 | 7/2002 | Gong et al. | |
| 2002/0137031 A1 | 9/2002 | Wolber | |
| 2002/0150966 A1 | 10/2002 | Muraca | |
| 2002/0159642 A1 | 10/2002 | Whitney | |
| 2003/0055619 A1 | 3/2003 | Singarajan et al. | |
| 2004/0122708 A1 | 6/2004 | Avinash et al. | |
| 2004/0122790 A1 | 6/2004 | Walker et al. | |
| 2004/0162852 A1 | 8/2004 | Qu et al. | |
| 2005/0081188 A1 | 4/2005 | Kumar et al. | |
| 2006/0277016 A1 | 12/2006 | Kouchi et al. | |
| 2006/0287106 A1 | 12/2006 | Jensen | |
| 2007/0118399 A1 | 5/2007 | Avinash et al. | |
| 2007/0156692 A1 | 7/2007 | Rosewarne | |
| 2007/0162411 A1 | 7/2007 | Kupershmidt et al. | |
| 2008/0103995 A1 | 5/2008 | Mohamed et al. | |
| 2008/0144124 A1 | 6/2008 | Samadani et al. | |

(Continued)

FOREIGN PATENT DOCUMENTS

| | | |
|---|---|---|
| JP | 2002-528095 A | 9/2002 |
| JP | 2004/152035 A | 5/2004 |

(Continued)

OTHER PUBLICATIONS

PCT Notification of Transmittal of the International Search Report and the Written Opinion of the International Searching Authority, or the Declaration, mailed May 6, 2009, Application No. PCT/US 06/36058, 9 pages.

(Continued)

*Primary Examiner* — Eric S Dejong
(74) *Attorney, Agent, or Firm* — Weaver Austin Villeneuve & Sampson LLP

(57) ABSTRACT

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure. According to various embodiments, methods, systems and interfaces for associating experimental data, features and groups of data related by structure and/or function with chemical, medical and/or biological terms in an ontology or taxonomy are provided. According to various embodiments, methods, systems and interfaces for filtering data by data source information are provided, allowing dynamic navigation through large amounts of data to find the most relevant results for a particular query.

21 Claims, 25 Drawing Sheets

(56) References Cited

U.S. PATENT DOCUMENTS

| | | |
|---|---|---|
| 2008/0147451 A1 | 6/2008 | Schnack |
| 2008/0155018 A1 | 6/2008 | Fortier et al. |
| 2009/0049019 A1 | 2/2009 | Su et al. |
| 2009/0238465 A1 | 9/2009 | Lee et al. |
| 2010/0172567 A1 | 7/2010 | Prokoski |
| 2010/0277650 A1 | 11/2010 | Matsuzaki |
| 2010/0305806 A1 | 12/2010 | Hawley |
| 2010/0318528 A1 | 12/2010 | Kupershmidt et al. |
| 2011/0119209 A1 | 5/2011 | Kirshenbaum et al. |
| 2011/0263445 A1 | 10/2011 | Wolber |
| 2013/0166320 A1 | 6/2013 | Kupershmidt et al. |
| 2013/0166599 A1 | 6/2013 | Kupershmidt et al. |

FOREIGN PATENT DOCUMENTS

| | | |
|---|---|---|
| JP | 2004/535612 A | 11/2004 |
| JP | 2005/518793 A | 6/2005 |
| JP | 2005/309836 A | 11/2005 |
| WO | 00/24936 | 5/2000 |
| WO | 01/55951 | 8/2001 |
| WO | 2007/075488 | 7/2007 |
| WO | 2009/039425 | 3/2009 |
| WO | 2009/520278 | 5/2009 |
| WO | 2009/111581 | 9/2009 |

OTHER PUBLICATIONS

Raja, Alexandra, "Querying Microarray Databases," Masters Thesis, University of Texas, Published: Dec. 2005 [retrieved by Foreign Examiner on Apr. 21, 2009]. Retrieved from the Internet: <URL: https://dspace.uta.edu/bitstream/10106/251/1/umi-uta-1117.pdf>, 163 pages.
Final Office Action mailed Jul. 28, 2011 for U.S. Appl. No. 12/234,435.
Kupershmidt, Ilya, et al., U.S. Appl. No. 11/641,539 titled, "System and Method for Scientific Information Knowledge Management," filed Dec. 18, 2006.
Su, Qiaojuan, et al., U.S. Appl. No. 12/234,435 titled, "Directional Expression-Based Scientific Information Knowledge Management," filed Sep. 19, 2008.
PCT International Search Report and Written Opinion of the International Searching Authority mailed Mar. 20, 2008, Application No. PCT/US2006/048067.
PCT International Search Report and Written Opinion of the International Searching Authority mailed Dec. 4, 2008, Application No. PCT/US08/77097.
Office Action mailed Sep. 29, 2010 from U.S. Appl. No. 11/641,539.
Final Office Action mailed May 11, 2011 from U.S. Appl. No. 11/641,539.
Office Action mailed Dec. 22, 2010 from U.S. Appl. No. 12/234,435.
Kupershmidt, et al., U.S. Appl. No. 12/796,545, titled "Sequence-Centric Scientific Information Management," filed Jun. 8, 2010.
Supplemental European Search Report mailed Mar. 23, 2012, Application No. EP 06 84 7688.6.
Barrett, T., et al., "NCBI GEO: Mining Millions of Expression Profiles—Database and Tools," vol. 33, Nucleic Acids Research, Database Issue, 2005, pp. D562-D0566.
Shah, S. P., et al., "Atlas—a Data Warehouse for Integrative Bioinformatics," London GB, vol. 6, No. 34, Feb. 21, 2005, pp. 1-16.
Liu, W., et al. "Rank-Based Algorithms for Analysis of Microarrays," Proceedings of SPIE, US, vol. 4266, Jun. 1, 2001, pp. 56-67.
Kupershmidt, et al., "Ontology-Based Meta-Analysis of Global Collections of High-Throughput Public Data," PLOS ONE, vol. 5, No. 9, Sep. 2010, pp. 1-13.
Office Action dated Jan. 26, 2012 for U.S. Appl. No. 12/796,545.
Japanese Office Action mailed May 22, 2012, Application No. 2008-545870.
Rashef, et al., "Detecting Novel Associations in Large Data Sets," *Science*, 2011, vol. 334, pp. 1518-1524.
Notice of Allowance mailed Jul. 19, 2012 from U.S. Appl. No. 11/641,539.
Ganter, et al. "Development of a large-scale chemogenomics database to improve drug candidate selection and to understand mechanisms of chemical toxicity and action," *Journal of Biotechnology*, vol. 119, 2005, pp. 219-244.
Lamb, et al., "The Connectivity Map: using gene-expression signatures to connect small molecules, genes, and disease," *Science*, 2006, vol. 313, pp. 1929-1935.
Engreit, et al., "ProfileChaser: searching microarray repositories based on genome-wide patterns of differential expression," 10(11):R130, 2011, 1;27(23), pp. 3317-3318.
Wu, et al, "BioGPS: an extensible and customizable portal for querying and organizing gene annotation resources," *Genome Biol.*, 2009, 10(11):R130, 12 pages.
Notice of Allowance mailed Jul. 19, 2012, issued in U.S. Appl. No. 11/641,539.
Notice of Allowance mailed Sep. 28, 2012, issued in U.S. Appl. No. 12/234,435.
Final Office Action dated Oct. 12, 2012, issued in U.S. Appl. No. 12/796,545.
Office Action dated Sep. 23, 2013, issued in U.S. Appl. No. 12/796,545.
Office Action dated Jul. 9, 2014, issued in U.S. Appl. No. 12/796,545.
Office Action dated Oct. 10, 2013, issued in U.S. Appl. No. 13/621,756.
Final Office Action dated Jul. 29, 2014, issued in U.S. Appl. No. 13/621,756.

HOME | LIBRARY EXPLORER | DATA IMPORT

NEXTBIO> Gata2                    Search        Settings/Preferences
                                                   My NextBio Gene: GATA2 [Homo Sapiens]

Annotations                Switch to full inspector view
       Show More Annotations Summary of Significant Results    Provide Search Stats Here

Tissues/Organs    Diseases         Treatments
■ Liver              ■ Breast cancer      ■ Erlotinib
■ Lung               ■ Lung cancer        ■ Tamoxifen
■ Macrophages        ■ Parkinson's        ■ Estradiol
■ Spleen             ■ Alzheimer's        ■ Paclitaxel
...                                        Show More Groups Individual Study Results    FILTER Breast cancer in large population-based cohort of Swedish patients
tissue material was collected from all breast cancer patients
receiving surgery at Karolinska Hospital from 1994 -
NextBio Library/Stem cells and Differentiation/...View Study Details
        p-value = 5.5E-29

Radiation exposure induced papillary thyroid carcinoma
We compared the expression profiles of papillary thyroid tumors from
Chernobyl Tissues Bank (CTB)...no history of exposure to radiations...
NextBio Library/Stem cells and Differentiation...View Study Details
        p-value = 2.5E-24

Broad Connectivity Map—Clinical compounds signatures
A reference collection of genome-wide transcriptional expression data
for bioactive small molecules..contains data for 164 distinct small molecules.
NextBio Library/Stem cells and Differentiation...View Study Details
        p-value = 4.4E-12

Additional links

| HOME | LIBRARY EXPLORER | DATA IMPORT |                    Settings/Preferences
                                                                  My NextBio NEXTBIO>  [ mapk signaling pathway ]   Search Biogroup:   MAPK Pathway  [Homo Sapiens]

[ Switch to inspector view ]

Annotations                    Show More Annotations

Summary of Significant Results    Provide Search Stats Here

Tissues/Organs   Diseases      Treatments
■ Liver              ■ Breast cancer   ■ Erlotinib
■ Lung               ■ Lung cancer     ■ Tamoxifen
■ Macrophages        ■ Parkinson's     ■ Estradiol
■ Spleen             ■ Alzheimer's     ■ Paclitaxel
...                  ...               Show More Groups Individual Study Results    FILTER Breast cancer in large population - based cohort of Swedish patients ...
Tissue material was collected from all breast cancer patients
receiving surgery at Karolinska Hospital from 1994 - 1996   View Study Details;
NextBio Library/Stem cells and Differentiation/...
         p- value = 5.5E- 29

Radiation exposure - induced papillary thyroid carcinoma
We compared the expression profiles of papillary thyroid tumors from
Chernobyl Tissues Bank (CTB) ... no history of exposure to radiations....
NextBio Library/Stem cells and Differentiation...    View Study Details;
         p- value = 2.5E- 24

Broad Connectivity Map - Clinical compounds signatures
A reference collection of genome - wide transcriptional expression data
for bioactive small molecules.... contains data for 164 distinct small molecules ...
NextBio Library/Stem cells and Differentiation...  View Study Details ;
         p- value = 4.4E- 12
...
...

(Additional links)

Feature – Concept Scoring Table

$$\begin{array}{cccc} F_1-C_1 & F_1-C_2 & \cdots & F_1-C_m \\ F_2-C_1 & F_2-C_2 & \cdots & F_2-C_m \\ \vdots & \vdots & \ddots & \vdots \\ F_n-C_1 & F_n-C_2 & \cdots & F_n-C_m \end{array}$$

*Sort along a column to find top scoring feature for a concept*

*Sort along a row to find top scoring concepts for a feature*

| HOME | LIBRARY EXPLORER | DATA IMPORT | Settings/Preferences |

NEXTBIO> [ rapamycin ] Search   My NextBio

Compound: Rapamycin

Annotations/Source URL
Show More Annotations

Summary of Significant Results  Provide Search Stats Here

Genes           Biogroups
■ Gata2            ■ Cell cycle
■ Cox2             ■ mTOR pathway ←— 1205
■ Pou1f1           ■ Apoptosis
■ Pou1f2           ■ MAPK pathway
         More

Individual Study Results    FILTER

Rapamycin–treated Breastcancer patients...
Tissue material was collected from all breast cancer patients
receiving rapamycintherapy in early clinical trials
NextBioLibrary/Oncology... View Study Details;

MCF7 cell lines treated with different doses of rapamycin
We compared the expression profiles of MCF7 cell lines
treated with rapamycin and vehicle controls...
NextBioLibrary/Stem cells and Differentiation.. View Study Details;

Broad Connectivity Map– compounds database
A reference collection of genomewide transcriptional expression data
for bioactive small molecules. contains data for 164 distinct small molecules.
NextBioLibrary/Stem cells and Differentiation.. View Study Details;

...
...

Additional links

My nextbio   data import   community                                           sign in | register for free NEXTBIO > ESR1                    [ Search ]

gene > ESR1   see other results

The estrogen receptor (ESR) is a ligand-activated transcription factor composed of several domains important for hormone binding, DNA binding, and activation of transcription. Alternative splicing res... view more >> sources of data and associations for experiments organisms         data types
 □ human          □ gene expression
 □ mouse          □ phenotypic
 □ rat            □ therapeutic normal tissues     diseases              treatments
 □ Region of myocardium  □ Breast cancer   □ Dienestrol
 □ Myometrium            □ Migraine        □ Estrone
 □ Cervix of uterus      □ Lymph node metastases  □ Clomifene
 □ Uterine tube          □ Papillary cystadenocarcin...  □ Estrone sodium sulfate
 □ Neck                  □ Basal cell carcinoma  □ Acapodene
 □ Peritoneum            □ Vulva Cancer    □ Diethylstilbestrol see more associations >> individual study results for : ESR1 experiments (430)  literature (22,992)  clinical trials (60)  full text (7,913)      show filter ⊞ DrugBank
The DrugBank database is a unique bioinformatics and cheminformatics resource that combines detailed drug (i.e. chemical, pharmacological and pharmace...
NextBio Libarary/Oncology  view study details >>
homo sapiens ⊞ Estrogen receptors mutants affecting ERE binding
This SuperSeries is composed of the following subset Series:
NextBio Libaray/Atlas - Organs, tissues and cell types   view study details >>
homo sapiens ⊞ MAP kinase activation cascades in mouse heart - ERK, p38 and JNK
Three major MAP kinase signalling cascades, ERK, p38 and JNK, play significant roles in the development of cardiac hypertrophy and heart failure in res...
NextBio Libaray/Cardiovascular disorders  view study details >>
mus musculus □ bookmark this page
✉ forward this page
✉ e-mail feedback
📄 create a report NextBio is a new search engine and collaboration platform serving the life sciences research community.

Used by over 130,000 researchers and clinicians worldwide.

NextBio Enterprise Solution
learn more >>

NextBio Webinar
register now >>

Figure 14A

Authority Levels

Feature – Concept

| | F1 | F2 | F3 | F4 | ... | Fm |
|---|---|---|---|---|---|---|
| C1 | V | V | E | HC | ... | HC |
| C2 | E | E | HC | HC | ... | E |
| C3 | V | HC | null | HC | ... | E |
| C4 | HC | HC | null | E | ... | V |
| Cn | HC | E | HC | E | ... | E |

Feature Set – Concept

| | FS1 | FS2 | FS3 | FS4 | ... | FSm |
|---|---|---|---|---|---|---|
| C1 | HC | E | HC | E | ... | null |
| C2 | V | null | E | V | ... | V |
| C3 | E | HC | HC | V | ... | E |
| C4 | E | E | E | E | ... | V |
| Cn | HC | HC | HC | HC | ... | E |

Feature Group – Concept

| | FG1 | FG2 | FG3 | FG4 | ... | FGm |
|---|---|---|---|---|---|---|
| C1 | E | V | HC | V | ... | HC |
| C2 | HC | null | HC | E | ... | HC |
| C3 | E | E | V | V | ... | null |
| C4 | HC | HC | V | E | ... | HC |
| Cn | V | HC | null | HC | ... | E |

Figure 18B

CATEGORIZATION AND FILTERING OF SCIENTIFIC DATA

CROSS REFERENCE TO RELATED APPLICATIONS

This application claims benefit under 35 U.S.C. §119(e) of the following U.S. Provisional Patent Applications: U.S. Provisional Patent Application No. 61/033,673, titled "Meta-Analysis And Clustering Of Search Results In Systems And Methods For Scientific Knowledge Information Management," filed Mar. 4, 2008 and U.S. Provisional Patent Application No. 61/089,834, titled "Categorization and Filtering of Scientific Data by Data Source," filed Aug. 18, 2008. Both of these applications are incorporated by reference herein in their entireties. This application is also a continuation-in-part of and claims priority to U.S. patent application Ser. No. 11/641,539, published as U.S. Patent Publication 20070162411, titled "System And Method For Scientific Information Knowledge Management," filed Dec. 18, 2006, which in turn claims benefit under 35 U.S.C. §119(e) of U.S. Provisional Patent Application 60/750,829, filed Dec. 16, 2005. These applications are incorporated by reference herein in their entireties.

BACKGROUND OF THE INVENTION

The present invention relates generally to methods, systems and apparatus for storing and retrieving biological, chemical and medical information. Research in these fields has increasingly shifted from the laboratory bench to computer-based methods. Public sources such as NCBI (National Center for Biotechnology Information), for example, provide databases with genetic and molecular data. Between these and private sources, an enormous amount of data is available to the researcher from various assay platforms, organisms, data types, etc. As the amount of biomedical information disseminated grows, researchers need fast and efficient tools to quickly assimilate new information and integrate it with pre-existing information across different platforms, organisms, etc. Researchers also need tools to quickly navigate through and analyze diverse types of information.

SUMMARY OF THE INVENTION

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure. Embodiments of the invention provide methods, systems and interfaces for associating experimental data, features and groups of data related by structure and/or function with chemical, medical and/or biological terms in an ontology or taxonomy. Embodiments of the invention also provide methods, systems and interfaces for filtering data by data source information, allowing dynamic navigation through large amounts of data to find the most relevant results for a particular query.

Embodiments of the invention provide methods for associating experimental data, features and groups of data related by structure and/or function with chemical, medical and/or biological terms in an ontology or taxonomy. Provided are methods of efficiently correlating various types of data (e.g., a gene, a compound, an experimental study, a group of genes, or other features associated by structure and/or function) with tags (also referred to as concepts) to identify the most relevant tags for that piece of data. In certain embodiments, the data analyzed by the methods described are typically noisy and imperfect. The methods filter out noisy tags to make the predictions. Also provided are methods of querying various types of data in a database (including features, feature sets, feature groups, and tags or concepts) to produce a list of the most relevant or significant concepts in the database in response to the query.

Embodiments of the invention provide methods of filtering data by data source information, allowing dynamic navigation through large amounts of data to find the most relevant results for a particular query. Also provided are methods of determining and presenting data authority levels for a particular query. In certain embodiments, the methods assign authority levels based on other data in a Knowledge Base of scientific information.

One aspect of the invention relates to methods for correlating chemical and/or biological concepts with other information in a knowledge base, said knowledge base comprising 1) a taxonomy of biological and/or chemical concepts arranged in a hierarchical structure comprising at least one top-level category, 2) a plurality of feature sets and/or feature groups, each feature set comprising at least one feature of chemical or biological information and associated statistical information and each feature group comprising a list of related features wherein at least some of said feature sets and feature groups are associated with one or more concepts in the taxonomy, wherein the methods involve: for each of a plurality or all of the concepts in the taxonomy, identifying feature sets that contribute to scoring the concept under consideration by identifying all feature sets associated with the concept under consideration and/or its child concepts; receiving pre-computed correlation scores and/or rank scores between the contributing feature sets and other information in the knowledge base; and calculating a score indicating correlation between the concept under consideration and other information in the knowledge base based on the precomputed correlations and/or rank scores. In certain embodiments, computer program products and computer systems for implementing the methods are also provided.

In certain embodiments, identifying feature sets that contribute to scoring the concept under consideration further comprises filtering the identified feature sets to remove at least some less relevant feature sets. The methods may also involve receiving pre-computed correlation scores and/or rank scores between the contributing feature sets and other information in the knowledge base comprises receiving pre-computed correlation scores indicating the correlation between the contributing feature sets and all or at least some of the other feature sets in the knowledge base. In certain embodiments, receiving pre-computed correlation scores and/or rank scores between the contributing feature sets and other information in the knowledge base comprises receiving pre-computed correlation scores indicating the correlation between the contributing feature sets and all or at least some of the feature groups in the knowledge base. In certain embodiments, receiving pre-computed correlation scores and/or rank scores between the contributing feature sets and other information in the knowledge base comprises receiving normalized ranks of all or at least some of the features in the contributing feature sets. In certain embodiments, receiving pre-computed correlation scores and/or rank scores between the contributing feature sets and other information in the knowledge base comprises receiving pre-computed correlation scores indicating the correlation between the contributing feature sets and feature sets that contribute to the scoring of all or at least some of the other concepts in the knowledge base. Also In certain embodiments, the methods further comprise generating one or more feature sets from raw data from one or more samples, wherein the raw data includes information on one or more features with indications of one or more of: differential expression, abundance of said features, responses of said features to a treatment or stimulus, and effects of said features on biological systems. In certain embodiments, the methods further involve importing the one or more generated feature sets into the knowledge base. According to various embodiments, the methods further involve displaying to a user a list of concepts relevant to identified information in the knowledge base.

Another aspect of the invention relates to computer-implemented methods of correlating chemical and/or biological concepts in a knowledge base, said knowledge base comprising 1) a taxonomy of biological and/or chemical concepts arranged in a hierarchical structure comprising at least one top-level category, 2) a plurality of feature sets each comprising at least one feature of chemical or biological information and associated statistical information wherein at least some of said feature sets and feature groups are associated with one or more concepts in the taxonomy, said method involving: for each of a plurality or all of the concepts in the taxonomy, identifying feature sets that contribute to scoring the concept under consideration by identifying all feature sets associated with the concept under consideration and/or its child concepts; and for all or a plurality of unique concept pairs in the knowledge base, receiving correlation scores indicating the pair-wise correlations of the feature sets that contribute to the concept under consideration with the feature sets of at least one or other concept in the knowledge base and calculating a score indicating the correlation between the concepts in the pair based on the pair-wise correlation scores.

Another aspect of the invention relates to a computer-implemented method of conducting a query in a knowledge base of chemical and/or biological information and comprising a plurality of feature sets and/or feature groups and a taxonomy, each feature set comprising at least one feature of chemical or biological information and associated statistical information, each feature group comprising a list of related features, and the taxonomy comprising chemical and/or biological concepts arranged in a hierarchical structure having at least one top level category; the method involving receiving a query identifying one or more of said feature sets or feature groups, wherein the query is received from a user input to a computer system; using precomputed scores between the one or more feature sets or feature groups and concepts in the taxonomy to determine the most relevant concepts in response to said query; and presenting the user with a ranked list of concepts as determined by using the precomputed scores.

In certain embodiments, the at least one top level category comprises at least one of the group consisting of tissues or organs, diseases, and treatments. In certain embodiments, presenting the user with a ranked list of concepts comprises presenting the user with a ranked list of concepts for each top level category.

Another aspect of the invention relates to a computer-implemented method of conducting a query in a knowledge base of chemical and/or biological information and comprising a plurality of feature sets and a taxonomy, each feature set comprising at least one feature of chemical or biological information and associated statistical information and the taxonomy comprising chemical and/or biological concepts arranged in a hierarchical structure having at least one top level category; the method comprising receiving a query identifying one or more of said features, wherein the query is received from a user input to a computer system; using normalized ranks of features in feature sets associated with concepts in the taxonomy to determine the most relevant concepts in response to said query; and presenting the user with a ranked list of concepts as determined by using the normalized ranks.

In certain embodiments, the at least one top level category comprises at least one of the group consisting of tissues or organs, diseases, and treatments. In certain embodiments, presenting the user with a ranked list of concepts comprises presenting the user with a ranked list of concepts for each top level category.

Another aspect of the invention relates to a method of conducting a query in a knowledge base of chemical and/or biological information and comprising a plurality of feature sets and a taxonomy, each feature set comprising at least one feature of chemical or biological information and associated statistical information and the taxonomy comprising chemical and/or biological concepts arranged in a hierarchical structure having at least one top level category; the method comprising: receiving a query identifying one or more of said concepts, wherein the query is received from a user input to a computer system; using pre-computed scores indicating the correlation between concepts in the taxonomy to determine the most relevant concepts in response to said query; and presenting the user with a ranked list of concepts as determined by using the pre-computed scores.

Another aspect of the invention relates to a computer-implemented method of correlating chemical and/or biological concepts with other information in a knowledge base, said knowledge base comprising 1) a taxonomy of biological and/or chemical concepts arranged in a hierarchical structure comprising at least one top-level category, 2) a plurality of feature sets and/or feature groups, each feature set comprising at least one feature of chemical or biological information and associated statistical information and each feature group comprising a list of related features wherein at least some of said feature sets and feature groups are associated with one or more concepts in the taxonomy, said method comprising: for each of a plurality or all of the concepts in the taxonomy, identifying feature sets that contribute to scoring the concept under consideration by identifying all feature sets associated with the concept under consideration and/or its child concepts; receiving pre-computed correlation scores and/or rank scores between the contributing feature sets and other information in the knowledge base; and calculating a score indicating correlation between the concept under consideration and other information in the knowledge base based on the precomputed correlations and/or rank scores.

Another aspect of the invention relates to a knowledge base for storing, managing, organizing and querying data comprising scientific experiment information, said knowledge base comprising: a plurality of feature sets, each feature set comprising at least one feature and associated statistical information; a taxonomy comprising a list of tags arranged in a hierarchical structure; and a concept scoring table comprising information about the correlation between at least some of the tags in the taxonomy and at least some the feature and/or feature sets.

In certain embodiments, knowledge base includes one or more feature groups, each feature group comprising a list of features related by a common biological property. In certain embodiments, the concept scoring table further comprises information about the correlation between at least some of the tags in the taxonomy and at least some the feature groups. In certain embodiments, the concept scoring table further comprises information about the correlation between at least some of the concepts in the taxonomy. According to various embodiments, the concept scoring table is partitioned by at least one of data type, organism of origin and data authority level.

Another aspect of the invention relates to computer-implemented methods of conducting a query in a knowledge base of chemical and/or biological information and comprising a plurality of feature sets and/or feature groups, each feature set comprising at least one feature of chemical or biological information and associated statistical information as derived from chemical or biological experimental data and each feature group comprising a list of related features, the method comprising: receiving a query identifying one or more of said feature sets or feature groups, wherein the query is received from a user input to a computer system; determining correlations between the identified feature sets or feature groups and other content in the knowledge base; presenting the user with results comprising a ranked list of feature sets, wherein a ranking of a resulting feature set indicates the degree of correlation to the identified feature sets or feature groups; and presenting the user with an indication of data sources of the experimental data associated with the resulting feature sets. According to various embodiments, the data sources are selected from at least one of data type, organism of origin and authority level.

Another aspect of the invention relates to computer-implemented methods of providing data to a knowledge base of scientific information, said knowledge base comprising 1) a taxonomy of biological and/or chemical concepts arranged in a hierarchical structure comprising at least one top-level category, 2) a plurality of feature sets and/or feature groups, each feature set comprising at least one feature of chemical or biological information and associated statistical information and each feature group comprising a list of related features wherein at least some of said feature sets and feature groups are associated with one or more concepts in the taxonomy, the method involving one or more of: (a) receiving raw data from one or more samples, wherein the raw data includes information on one or more features with indications of one or more of: differential expression, abundance of said features, responses of said features to a treatment or stimulus, and effects of said features on biological systems; (b) producing an input feature set from the raw data; (c) correlating the input feature set against a plurality or all of the pre-existing feature sets in the knowledge base; (d) correlating the input feature set against a plurality or all of the concepts in the taxonomy; and (e) assigning a data authority level to a given concept-input feature set combination based on corroboration within the knowledge base that the given concept is significant to the experimental data represented by the input feature set.

Computer program products and computer systems for implementing any of the above methods are provided. These and other aspects of the invention are described further below with reference to the drawings.

BRIEF DESCRIPTION OF THE DRAWINGS

FIG. 7 presents a screen shot of a user interface window displaying results of a feature query.

FIG. 8 presents a screen shot of a user interface window displaying results of a Feature Group query.

FIG. 11 is a graphical depiction of a feature-concept scoring table in accordance with certain embodiments.

FIG. 12 presents a screen shot of a user interface window displaying results of a concept query.

FIG. 14A is a screen shot of a user interface window displaying results of a feature query.

FIG. 18B is a schematic representation of authority level (V, HC and E) assignments to each concept for each feature, Feature Set and Feature Group.

DETAILED DESCRIPTION

1. Introduction and Relevant Terminology

Figure 1:
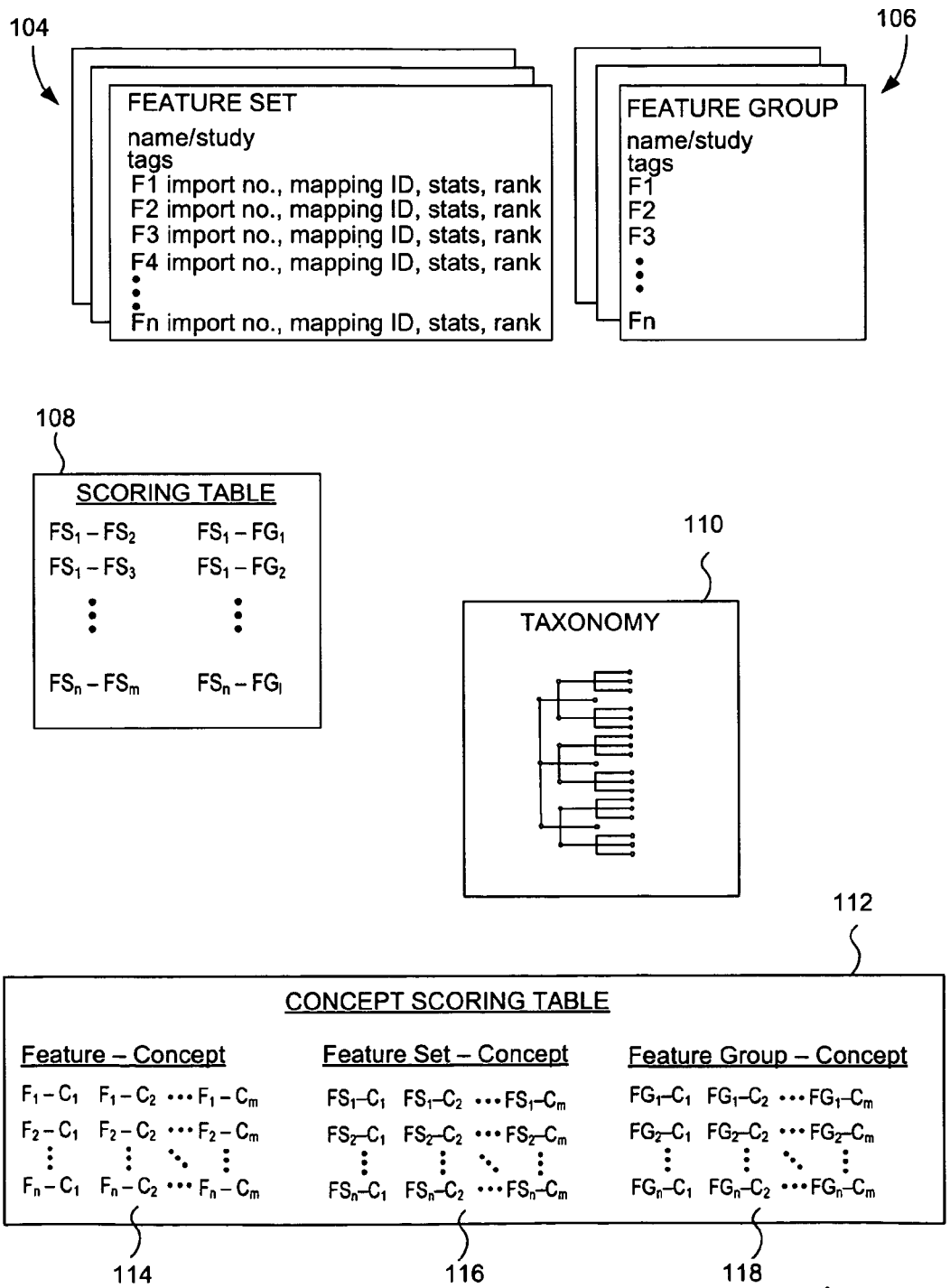
FIG. 1 is a representation of various elements in the Knowledge Base of scientific information according to various embodiments of the invention.

The present invention relates to methods, systems and apparatus for capturing, integrating, organizing, navigating and querying large-scale data from high-throughput biological and chemical assay platforms. It provides a highly efficient meta-analysis infrastructure for performing research queries across a large number of studies and experiments from different biological and chemical assays, data types and organisms, as well as systems to build and add to such an infrastructure.

While most of the description below is presented in terms of systems, methods and apparatuses that integrate and allow exploration of data from biological experiments and studies, the invention is by no means so limited. For example, the invention covers chemical and clinical data. In the following description, numerous specific details are set forth in order to provide a thorough understanding of the present invention. It will be apparent, however, that the present invention may be practiced without limitation to some of the specific details presented herein.

The following terms are used throughout the specification. The descriptions are provided to assist in understanding the specification, but do not necessarily limit the scope of the invention.

Raw data—This is the data from one or more experiments that provides information about one or more samples. Typically, raw data is not yet processed to a point suitable for use in the databases and systems of this invention. Subsequent manipulation reduces it to the form of one or more "feature sets" suitable for use in such databases and systems. The process of converting the raw data to feature sets is sometimes referred to as curation.

Most of the examples presented herein concern biological experiments in which a stimulus acts on a biological sample such as a tissue or cell culture. Often the biological experiment will have associated clinical parameters such as tumor stage, patient history, etc. The invention is not however limited to biological samples and may involve, for example, experiments on non-biological samples such as chemical compounds, various types of synthetic and natural materials, etc. and their effects on various types of assays (e.g., cancer cell line progression).

Whether working with biological or non-biological samples, the sample may be exposed to one or more stimuli or treatments to produce test data. Control data may also be produced. The stimulus is chosen as appropriate for the particular study undertaken. Examples of stimuli that may be employed are exposure to particular materials or compositions, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc. As suggested, a particularly important class of stimuli in the context of this invention is exposure to therapeutic agents (including agents suspected of being therapeutic but not yet proven to have this property). Often the therapeutic agent is a chemical compound such as a drug or drug candidate or a compound present in the environment. The biological impact of chemical compounds is manifest as a change in a feature such as a level of gene expression or a phenotypic characteristic.

As suggested, the raw data will include "features" for which relevant information is produced from the experiment. In many examples the features are genes or genetic information from a particular tissue or cell sample exposed to a particular stimulus.

A typical biological experiment determines expression or other information about a gene or other feature associated with a particular cell type or tissue type. Other types of genetic features for which experimental information may be collected in raw data include SNP patterns (e.g., haplotype blocks), portions of genes (e.g., exons/introns or regulatory motifs), regions of a genome of chromosome spanning more than one gene, etc. Other types of biological features include phenotypic features such as the morphology of cells and cellular organelles such as nuclei, Golgi, etc. Types of chemical features include compounds, metabolites, etc.

The raw data may be generated from any of various types of experiments using various types of platforms (e.g., any of a number of microarray systems including gene microarrays, SNP microarrays and protein microarrays, cell counting systems, High-Throughput Screening ("HTS") platforms, etc.). For example, an oligonucleotide microarray is also used in experiments to determine expression of multiple genes in a particular cell type of a particular organism. In another example, mass spectrometry is used to determine abundance of proteins in samples.

Feature set—This refers to a data set derived from the "raw data" taken from one or more experiments on one or more samples. The feature set includes one or more features (typically a plurality of features) and associated information about the impact of the experiment(s) on those features. At some point, the features of a feature set may be ranked (at least temporarily) based on their relative levels of response to the stimulus or treatment in the experiment(s) or based on their magnitude and direction of change between different phenotypes, as well as their ability to differentiate different phenotypic states (e.g., late tumor stage versus early tumor stage).

For reasons of storage and computational efficiency, for example, the feature set may include information about only a subset of the features or responses contained in the raw data. As indicated, a process such as curation converts raw data to feature sets.

Typically the feature set pertains to raw data associated with a particular question or issue (e.g., does a particular chemical compound interact with proteins in a particular pathway). Depending on the raw data and the study, the feature set may be limited to a single cell type of a single organism. From the perspective of a "Directory," a feature set belongs to a "Study." In other words, a single study may include one or more feature sets.

In many embodiments, the feature set is either a "bioset" or a "chemset." A bioset typically contains data providing information about the biological impact of a particular stimulus or treatment. The features of a bioset are typically units of genetic or phenotypic information as presented above. These are ranked based on their level of response to the stimulus (e.g., a degree of up or down regulation in expression), or based on their magnitude and direction of change between different phenotypes, as well as their ability to differentiate different phenotypic states (e.g., late tumor stage versus early tumor stage). A chemset typically contains data about a panel of chemical compounds and how they interact with a sample, such as a biological sample. The features of a chemset are typically individual chemical compounds or concentrations of particular chemical compounds. The associated information about these features may be EC50 values, IC50 values, or the like.

A feature set typically includes, in addition to the identities of one or more features, statistical information about each feature and possibly common names or other information about each feature. A feature set may include still other pieces of information for each feature such as associated description of key features, user-based annotations, etc. The statistical information may include p-values of data for features (from the data curation stage), "fold change" data, and the like. A fold change indicates the number of times (fold) that expression is increased or decreased in the test or control experiment (e.g., a particular gene's expression increased "4-fold" in response to a treatment). A feature set may also contain features that represent a "normal state", rather than an indication of change. For example, a feature set may contain a set of genes that have "normal and uniform" expression levels across a majority of human tissues. In this case, the feature set would not necessarily indicate change, but rather a lack thereof.

In certain embodiments, a rank is ascribed to each feature, at least temporarily. This may be simply a measure of relative response within the group of features in the feature set. As an example, the rank may be a measure of the relative difference in expression (up or down regulation) between the features of a control and a test experiment. In certain embodiments, the rank is independent of the absolute value of the feature response. Thus, for example, one feature set may have a feature ranked number two that has a 1.5 fold increase in response, while a different feature set has the same feature ranked number ten that has a 5 fold increase in response to a different stimulus.

Directional feature set—A directional feature set is a feature set that contains information about the direction of change in a feature relative to a control. Bi-directional feature sets, for example, contain information about which features are up-regulated and which features are down-regulated in response to a control. One example of a bi-directional feature set is a gene expression profile that contains information about up and down regulated genes in a particular disease state relative to normal state, or in a treated sample relative to non-treated. As used herein, the terms "up-regulated" and "down-regulated" and similar terms are not limited to gene or protein expression, but include any differential impact or response of a feature. Examples include, but are not limited to, biological impact of chemical compounds or other stimulus as manifested as a change in a feature such as a level of gene expression or a phenotypic characteristic.

Non-directional feature sets contain features without indication of a direction of change of that feature. This includes gene expression, as well as different biological measurements in which some type of biological response is measured. For example, a non-directional feature set may contain genes that are changed in response to a stimulus, without an indication of the direction (up or down) of that change. The non-directional feature set may contain only up-regulated features, only down-regulated features, or both up and down-regulated features, but without indication of the direction of the change, so that all features are considered based on the magnitude of change only.

Feature group—This refers to a group of features (e.g., genes) related to one another. As an example, the members of a feature group may all belong to the same protein pathway in a particular cell or they may share a common function or a common structural feature. A feature group may also group compounds based on their mechanism of action or their structural/binding features.

Index set—The index set is a set in the knowledge base that contains feature identifiers and mapping identifiers and is used to map all features of the feature sets imported to feature sets and feature groups already in the knowledge base. For example, the index set may contain several million feature identifiers pointing to several hundred thousand mapping identifiers. Each mapping identifier (in some instances, also referred to as an address) represents a unique feature, e.g., a unique gene in the mouse genome. In certain embodiments, the index set may contain diverse types of feature identifiers (e.g., genes, genetic regions, etc.), each having a pointer to a unique identifier or address. The index set may be added to or changed as new knowledge is acquired.

Knowledge base—This refers to a collection of data used to analyze and respond to queries. In certain embodiments, it includes one or more feature sets, feature groups, and metadata for organizing the feature sets in a particular hierarchy or directory (e.g., a hierarchy of studies and projects). In addition, a knowledge base may include information correlating feature sets to one another and to feature groups, a list of globally unique terms or identifiers for genes or other features, such as lists of features measured on different platforms (e.g., Affymetrix human HG_U133A chip), total number of features in different organisms, their corresponding transcripts, protein products and their relationships. A knowledge base typically also contains a taxonomy that contains a list of all tags (keywords) for different tissues, disease states, compound types, phenotypes, cells, as well as their relationships. For example, taxonomy defines relationships between cancer and liver cancer, and also contains keywords associated with each of these groups (e.g., a keyword "neoplasm" has the same meaning as "cancer"). Typically, though not necessarily, at least some of the data in the knowledge base is organized in a database.

Curation—Curation is the process of converting raw data to one or more feature sets (or feature groups). In some cases, it greatly reduces the amount of data contained in the raw data from an experiment. It removes the data for features that do not have significance. In certain embodiments, this means that features that do not increase or decrease significantly in expression between the control and test experiments are not included in the feature sets. The process of curation identifies such features and removes them from the raw data. The curation process also identifies relevant clinical questions in the raw data that are used to define feature sets. Curation also provides the feature set in an appropriate standardized format for use in the knowledge base.

Data import—Data import is the process of bringing feature sets and feature groups into a knowledge base or other repository in the system, and is an important operation in building a knowledge base. A user interface may facilitate data input by allowing the user to specify the experiment, its association with a particular study and/or project, and an experimental platform (e.g., an Affymetrix gene chip), and to identify key concepts with which to tag the data. In certain embodiments, data import also includes automated operations of tagging data, as well as mapping the imported data to data already in the system. Subsequent "preprocessing" (after the import) correlates the imported data (e.g., imported feature sets and/or feature groups) to other feature sets and feature groups.

Preprocessing—Preprocessing involves manipulating the feature sets to identify and store statistical relationships between pairs of feature sets in a knowledge base. Preprocessing may also involve identifying and storing statistical relationships between feature sets and feature groups in the knowledge base. In certain embodiments, preprocessing involves correlating a newly imported feature set against other feature sets and against feature groups in the knowledge base. Typically, the statistical relationships are pre-computed and stored for all pairs of different feature sets and all combinations of feature sets and feature groups, although the invention is not limited to this level of complete correlation.

In one embodiment, the statistical correlations are made by using rank-based enrichment statistics. For example, a rank-based iterative algorithm that employs an exact test is used in certain embodiments, although other types of relationships may be employed, such as the magnitude of overlap between feature sets. Other correlation methods known in the art may also be used.

As an example, a new feature set input into the knowledge base is correlated with every other (or at least many) feature sets already in the knowledge base. The correlation compares the new feature set and the feature set under consideration on a feature-by-feature basis by comparing the rank or other information about matching genes. A rank-based iterative algorithm is used in one embodiment to correlate the feature sets. The result of correlating two feature sets is a "score." Scores are stored in the knowledge base and used in responding to queries.

Study/Project/Library—This is a hierarchy of data containers (like a directory) that may be employed in certain embodiments. A study may include one or more feature sets obtained in a focused set of experiments (e.g., experiments related to a particular cardiovascular target). A Project includes one or more Studies (e.g., the entire cardiovascular effort within a company). The library is a collection of all projects in a knowledge base. The end user has flexibility in defining the boundaries between the various levels of the hierarchy.

Tag—A tag associates descriptive information about a feature set with the feature set. This allows for the feature set to be identified as a result when a query specifies or implicates a particular tag. Often clinical parameters are used as tags. Examples of tag categories include tumor stage, patient age, sample phenotypic characteristics and tissue types. In certain embodiments, tags may also be referred to as concepts.

Mapping—Mapping takes a feature (e.g., a gene) in a feature set and maps it to a globally unique mapping identifier in the knowledge base. For example, two sets of experimental data used to create two different feature sets may use different names for the same gene. Often herein the knowledge base includes an encompassing list of globally unique mapping identifiers in an index set. Mapping uses the knowledge base's globally unique mapping identifier for the feature to establish a connection between the different feature names or IDs. In certain embodiments, a feature may be mapped to a plurality of globally unique mapping identifiers. In an example, a gene may also be mapped to a globally unique mapping identifier for a particular genetic region. Mapping allows diverse types of information (i.e., different features, from different platforms, data types and organisms) to be associated with each other. There are many ways to map and some of these will be elaborated on below. One involves the search of synonyms of the globally unique names of the genes. Another involves a spatial overlap of the gene sequence. For example, the genomic or chromosomal coordinate of the feature in a feature set may overlap the coordinates of a mapped feature in an index set of the knowledge base. Another type of mapping involves indirect mapping of a gene in the feature set to the gene in the index set. For example, the gene in an experiment may overlap in coordinates with a regulatory sequence in the knowledge base. That regulatory sequence in turn regulates a particular gene. Therefore, by indirect mapping, the experimental sequence is indirectly mapped to that gene in the knowledge base. Yet another form of indirect mapping involves determining the proximity of a gene in the index set to an experimental gene under consideration in the feature set. For example, the experimental feature coordinates may be within 100 basepairs of a knowledge base gene and thereby be mapped to that gene.

Correlation—As an example, a new feature set input into the knowledge base is correlated with every other (or at least many) feature sets already in the knowledge base. The correlation compares the new feature set and the feature set under consideration on a feature-by-feature basis comparing the rank or other information about matching genes. A ranked based running algorithm is used in one embodiment (to correlate the feature sets). The result of correlating two feature sets is a "score." Scores are stored in the knowledge base and used in responding to queries about genes, clinical parameters, drug treatments, etc.

Correlation is also employed to correlate new feature sets against all feature groups in the knowledge base. For example, a feature group representing "growth" genes may be correlated to a feature set representing a drug response, which in turn allows correlation between the drug effect and growth genes to be made.

2. Knowledge Base

FIG. 1 shows a representation of various elements in the Knowledge Base of scientific information according to various embodiments of the invention. Examples of generation of or addition to some of these elements (e.g., Feature Sets and a Feature Set scoring table) are discussed in U.S. patent application Ser. No. 11/641,539 (published as U.S. Patent Publication 20070162411), referenced above. The Knowledge Base may also include other elements such as an index set, which is used to map features during a data import process. In FIG. 1, element 104 indicates all the Feature Sets in the Knowledge Base. As is described in the U.S. Patent Publication 20070162411, after data importation, the Feature Sets typically contain at least a Feature Set name and a feature table. The feature table contains a list of features, each of which is usually identified by an imported ID and/or a feature identifier. Each feature has a normalized rank in the Feature Set, as well as a mapping identifier. Mapping identifiers and ranks may be determined during the import process, e.g., as described in U.S. Patent Publication 20070162411 and then may be used to generate correlation scores between Feature Sets and between Feature Sets and Feature Groups. The feature table also typically contains statistics associated with each feature, e.g., p-values and/or fold-changes. One or more of these statistics can be used to calculate the rank of each feature. In certain embodiments, the ranks may be normalized. The Feature Sets may also contain an associated study name and/or a list of tags. Feature Sets may be generated from data taken from public or internal sources.

Element 106 indicates all the Feature Groups in the Knowledge Base. Feature Groups contain a Feature Group name, and a list of features (e.g., genes) related to one another. A Feature Group typically represents a well-defined set of features generally from public resources—e.g., a canonical signaling pathway, a protein family, etc. Unlike Feature Sets, the Feature Groups do not typically have associated statistics or ranks. The Feature Sets may also contain an associated study name and/or a list of tags.

Element 108 indicates a scoring table, which contains a measure of correlation between each Feature Set and each of the other Feature Sets and between each Feature Set and each Feature Group. In the figure, $FS_1$-$FS_2$ is a measure of correlation between Feature Set 1 and Feature Set 2, $FS_1$-$FG_1$ a measure of correlation between Feature Set 1 and Feature Group 1, etc. In certain embodiments, the measures are p-values or rank scores derived from p-values.

Figure 2:
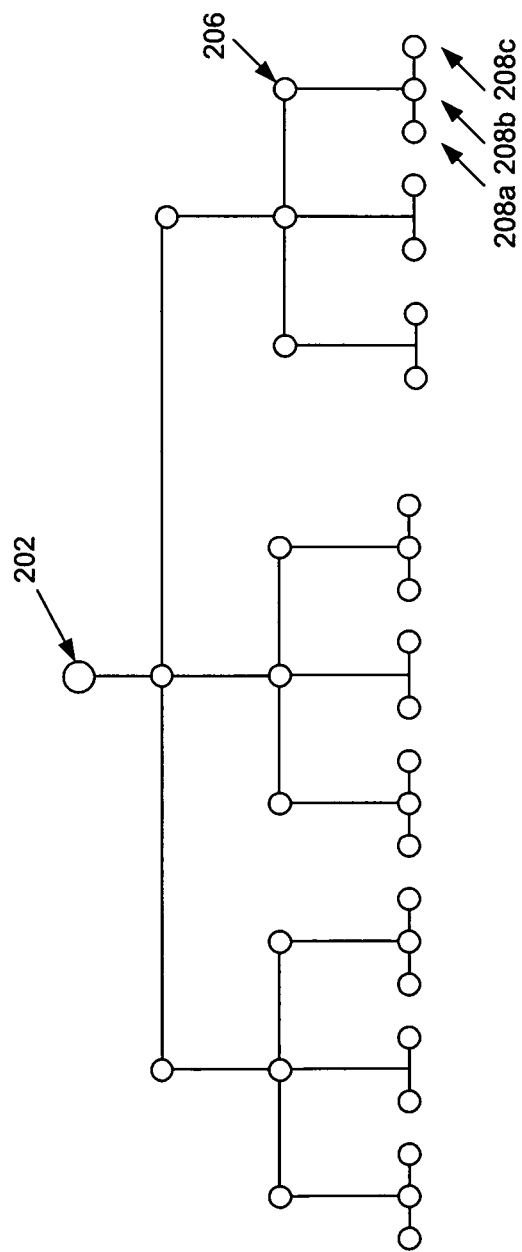
FIG. 2 is a representative schematic diagram of an ontology according to various embodiments of the invention.

Element 110 is a taxonomy or ontology that contains tags or scientific terms for different tissues, disease states, compound types, phenotypes, cells, and other standard biological, chemical or medical concepts as well as their relationships. The tags are typically organized into a hierarchical structure as schematically shown in the figure. An example of such a structure is Diseases/Classes of Diseases/Specific Diseases in each Class. The Knowledge Base may also contain a list of all Feature Sets and Feature Groups associated with each tag. The tags and the categories and sub-categories in the hierarchical structure are arranged in what may be referred to as concepts. A representative schematic diagram of an ontology is shown in FIG. 2. In FIG. 2, each node of the structure represents a medical, chemical or biological concept. Node 202 represents a top-level category, with children or sub-categories indicated by other nodes going down the tree, until the bottom-level concepts as indicated by node 208. In this manner, scientific concepts are categorized. For example, a categorization of stage 2 breast cancer may be: Diseases/Proliferative Diseases/Cancer/Breast Cancer/Stage 2 Breast Cancer, with disease the top-level category. Each of these—diseases, proliferative diseases, cancer, breast cancer and stage 2 breast cancer—is a medical concept that may be used to tag other information in the database. The taxonomy may be a publicly available taxonomy, such as the Medical Subject Headings (MeSH) taxonomy, Snomed, FMA (Foundation Model of Anatomy), PubChem Features, privately built taxonomies, or some combination of these. Examples of top-level categories include disease, tissues/organs, treatments, gene alterations, and Feature Groups.

Element 112 is a concept scoring table, which contains scores indicating the relevance of each concept or correlation of each concept with the other information in the database, such as features, Feature Sets and Feature Groups. In the embodiment depicted in FIG. 1, scores indicating the relevance of each concept in the taxonomy to each feature are shown at 114, scores indicating the relevance of each concept in the taxonomy to each Feature Set are shown at 116 and scores indicating the relevance of each concept in the taxonomy to each Feature Group are shown at 118. (As with the other elements represented in FIG. 1, the organizational structure of the concept scoring is an example; other structures may also be used to store or present the scoring.) In the figure, $F_1$-$C_1$ is a measure of relevance of Concept 1 to Feature 1, $FS_1$-$C_1$ a measure of relevance to Concept 1 to Feature Set 1; and $FG_1$-$C_1$ a measure of relevance to Concept 1 to Feature Group 1, etc. In certain embodiments, the concept scoring table includes information about the relevance or correlation of at least some concepts with each of all or a plurality of other concepts.

As discussed further below, the scores are stored for use in user queries to the Knowledge Base. Concept scoring allows a scientist querying the Knowledge Base to filter out the most relevant conditions for a query of interest. Users can quickly identify the top disease states, tissues, treatments and other entities associated with a query of interest. Also, as discussed below, concept scoring allows users to query concepts to find the most relevant features, Feature Sets and Feature Groups associated with the concept.

Generally, concept scoring involves i) identifying all Feature Sets having the concept under consideration, and ii) using the normalized rank of features within the identified Feature Sets or the pre-computed correlation scores of other Feature Sets or Feature Groups with the identified Feature Sets to determine a score indicating the relevance of the concept under consideration to each feature, Feature Set and Feature Group in the Knowledge Base. The concept scores can then be used to quickly identify the most relevant concepts for a particular feature, Feature Set or Feature Group. In certain embodiments, less relevant Feature Sets are removed prior to determining a score. For example, experiments done in a cell line may have little to do with the original disease tissue source for the cell line. Accordingly, in certain embodiments, Feature Sets relating to experiments done on this cell line may be excluded when computing scores for the disease concept.

2. Concept Scoring

Figure 3:
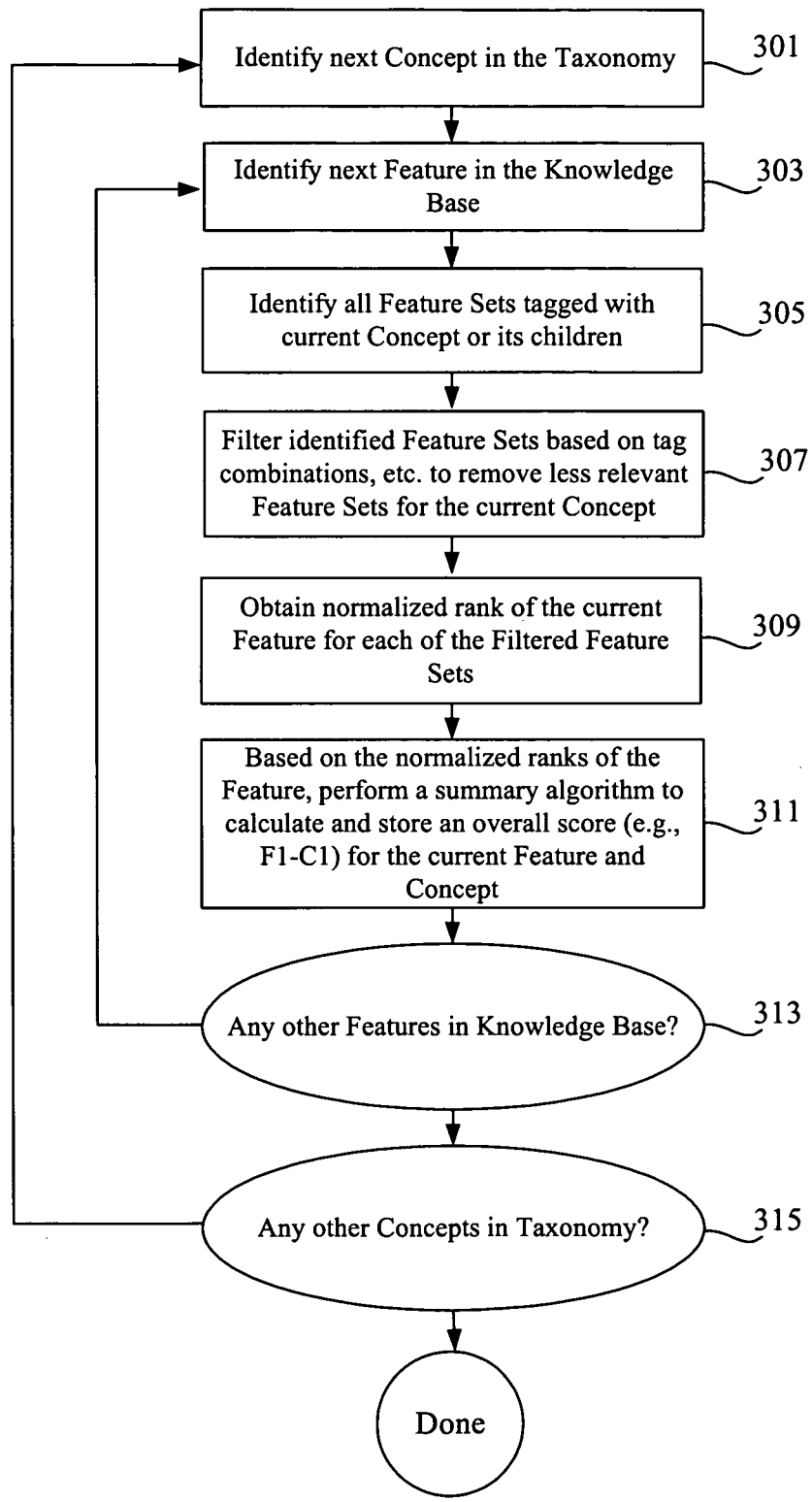
FIG. 3 is a process flow diagram depicting some operations of methods of determining the most relevant concepts for features according to certain embodiments.
Figure 4:
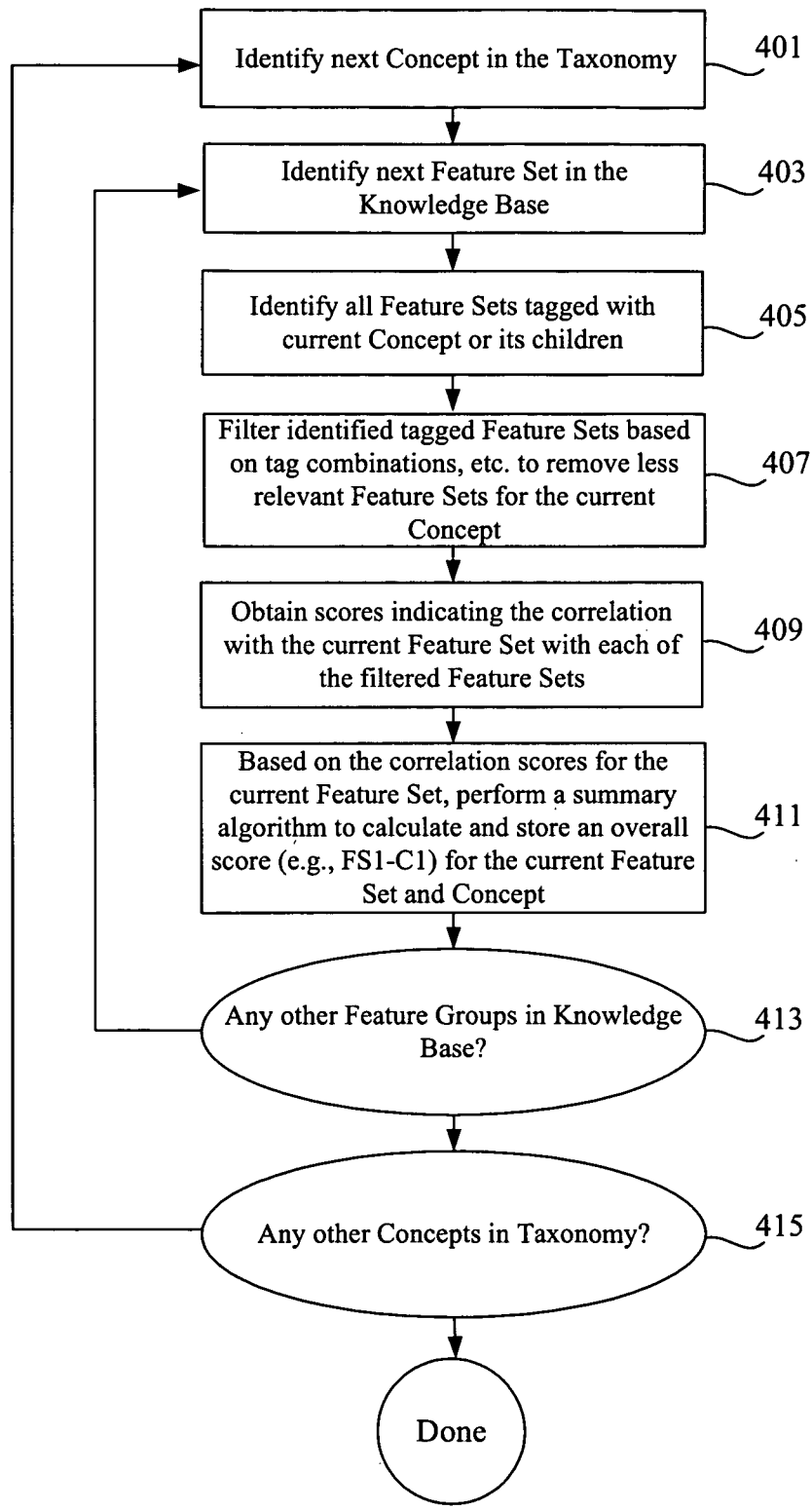
FIG. 4 is a process flow diagram depicting some operations of methods of determining the most relevant concepts for Feature Sets according to certain embodiments.
Figure 5:
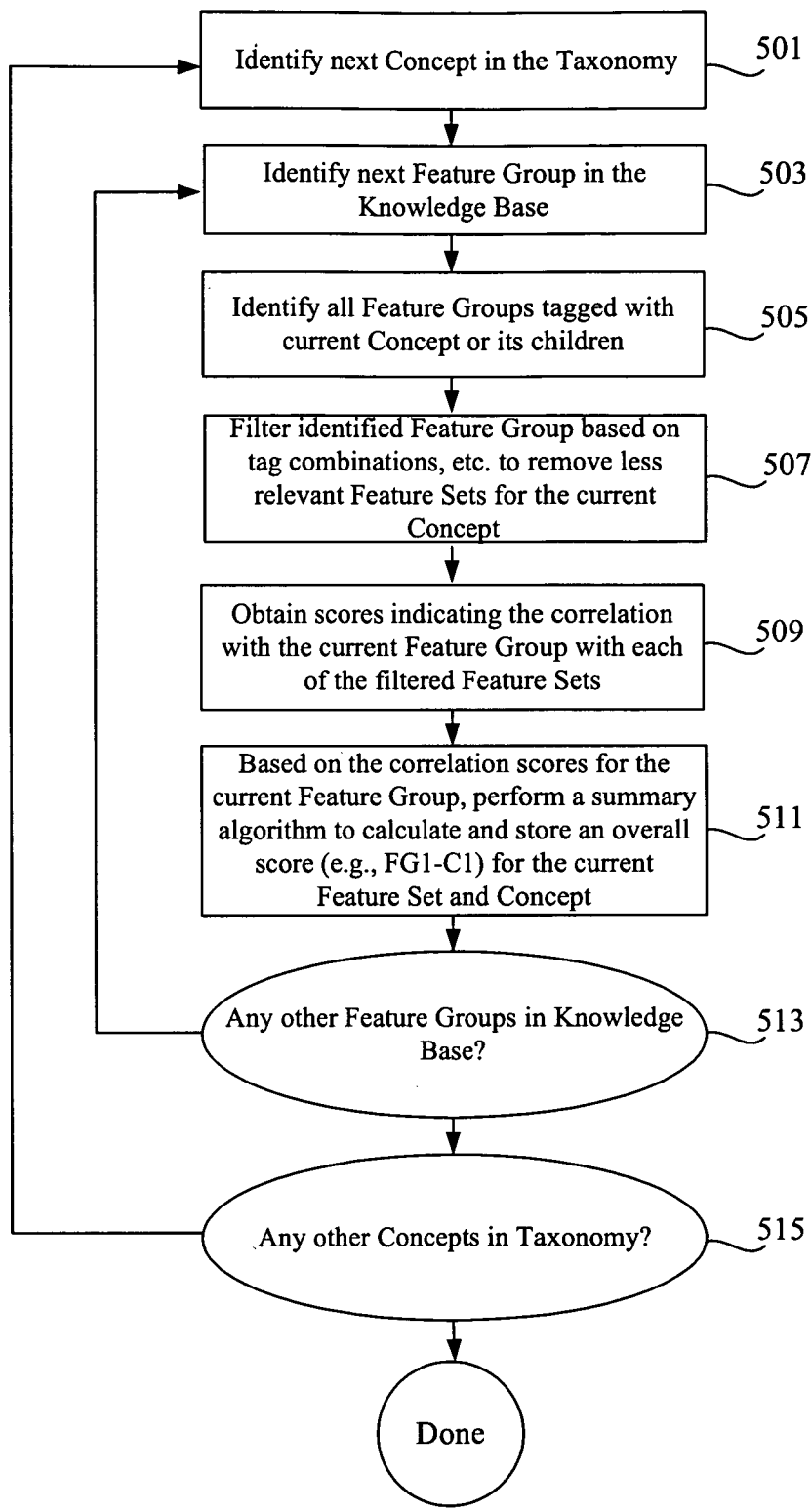
FIG. 5 is a process flow diagram depicting some operations of methods of determining the most relevant concepts for Feature Groups according to certain embodiments.

FIGS. 3-5 are process flow diagrams depicting operations of methods of determining the most relevant concepts for features (FIG. 3), Feature Sets (FIG. 4) and Feature Groups (FIG. 5) according to certain embodiments. These methods may be used, for example, to populate concept scoring tables as represented in FIG. 1, or some other form of storing concept scores. As discussed below, the stored scores may be used for response to user queries about a feature, Feature Set or Feature Group. Although FIGS. 3-5 discuss concept scoring as being performed prior to user queries, so that all Knowledge Base contains information about the most relevant concepts for each feature, Feature Set and Feature Group in the Knowledge Base, it will be apparent that the scoring may also take place on the fly in response to a user query that identifies one or more features, Feature Sets or Feature Groups. Once determined, this information may be stored as indicated in FIG. 1 for use in responding to future queries involving that feature, etc., or discarded.

FIG. 3 depicts a method of determining the relevance of concepts to individual features such as genes, compounds, etc., in accordance with specific embodiments. As depicted, the process begins at an operation 301 where the system identifies a "next" concept in the taxonomy. Typically, the process will consider each concept in the taxonomy. The process next identifies a "next" feature in the Knowledge Base. See block 303. The process typically considers each feature of the Knowledge Base. The process typically determines a score for each possible pair of concept and feature, and so iterates over all possible combinations, as indicated by the two loops in FIG. 3. After setting the concept and feature for the current iteration, the process next identifies all Feature Sets that are tagged with 1) the current concept or 2) its' children concepts. So, for example, referring to FIG. 2, if the concept represented at node 206 is under consideration, all features sets tagged with this concept and/or one or more of the concepts represented at its child nodes 208a, 208b and 208c are identified. In a specific example, a Feature Set tagged only with the concept "stage 2 breast cancer," would be identified for the concept 'stage 2 breast cancer' as well for its' parent concept, "breast cancer."

As discussed further below, the identified Feature Sets are filtered to remove (or in certain embodiments, reweight) Feature Sets that are less relevant to the concept or that would skew the results. After filtering the identified Feature Sets, the normalized rank of the current feature is obtained for each of the filtered Feature Sets, i.e., the Feature Sets remaining after removing the less relevant Feature Sets. See block 309. As described in U.S. Patent Publication 20070162411, features in a Feature Set are typically ranked based on the relative effect on or by the feature in the experiment(s) associated with the Feature Set. See, e.g., the schematic of FIG. 1 in which Feature Set 104 contains rankings of its features. In certain embodiments, obtaining the normalized ranks involves identifying, looking up, or receiving the rank of the feature in each of the filtered Feature Sets. So, for example, for a given feature $F_n$ and a given concept $C_m$, there may be 25 Feature Sets tagged with $C_m$ and/or at least one of its children concepts. Ten of those twenty-five Feature Sets may contain $F_n$. The normalized rank of $F_n$ in each of the Feature Sets is obtained: for example, 1/20, null, 4/8, etc., indicating a normalized rank of 1 of 20 features in the first filtered Feature Set, not present in the second Filtered Feature Set, a normalized rank of 4/8 features in the third filtered Feature Set, etc. (These are just examples of normalized ranks: ranks may be normalized using several criteria including Feature Set size, the number of features on a measurement platform for that Feature Set and any other relevant criteria. Use of normalized ranks allows the significance of a feature in one Feature Set to be compared with the significance of that feature in another Feature Set, regardless of the size of the relative size and other differences of the Feature Sets.) After these scores are obtained, an overall score $F_n$-$C_m$ indicating the relevance of the concept to the feature is obtained. See block 311. In certain embodiments, the criteria used for computation of the final feature-concept score includes the following attributes: normalized rank of that feature in each Feature Set tagged with that concept that passes "inclusion" criteria, the total number of Feature Sets containing this feature that pass the "inclusion" criteria and the total number of Feature Sets tagged with the concept.

The overall score $F_n$-$C_m$ is then stored, e.g., in a concept scoring table as shown in FIG. 1. Iteration over all features is controlled as indicated at decision block 313 and iteration over all concepts is controlled as indicated at decision block 315. As can be seen, in the method shown in FIG. 3, either iteration can be the inner or outer loop. The method shown in FIG. 3 iterates over all possible combination of concepts in the taxonomy and features in the knowledge base; however, in other embodiments, there may only be a subset of features and/or taxonomy concepts for which a concept score is calculated.

FIG. 4 depicts a method of determining the relevance of concepts to Feature Sets in accordance with specific embodiments. Similarly, to the feature concept scoring, the process begins at an operation 401 where the system identifies a "next" concept in the taxonomy. A "next" Feature Set is also identified at an operation 403. The process typically scores all possible Feature Set-concept pairs. Features Sets tagged with the current concept (and/or its children) are identified and filtered as discussed above with respect to FIG. 3. See blocks 405 and 407. Scores indicating the correlation between the current Feature Set (i.e., the Feature Set identified in operation 403) and each of the tagged and filtered Feature Sets are obtained. See block 409. In many embodiments, these scores are the correlation scores calculated as described in U.S. Patent Publication 20070162411. In many embodiments, they are obtained from a correlation matrix or table scoring such as table 106 depicted in FIG. 1. An overall score $FS_n$-$C_m$ indicating the relevance of the current concept to the current Feature Set is calculated based on the correlation scores obtained in operation 409. In certain embodiments, the criteria used for computation of the final feature set-concept score includes the following attributes: correlation score between Feature Set under study and each Feature Set tagged with a given concept that passes "inclusion" criteria, the total number of Feature sets providing non-zero correlation with the Feature Set of interest that pass the "inclusion" criteria and the total number of Feature Sets tagged with the concept. The overall score may then be stored for use in responding to user queries. The Feature Set and concept iterations are controlled by decision blocks 413 and 415.

FIG. 5 depicts a method of determining the relevance of concepts to Feature Groups in accordance with certain embodiments of the invention. The method mirrors that of concept scoring for Feature Sets depicted in FIG. 4, iterating over Feature Groups instead of Feature Sets. See blocks 501-515. Scores indicating the correlation between the current Feature Group and the filtered Feature Sets may be obtained from a correlation matrix or scoring table as depicted in FIG. 1.

Concept scoring for features, Feature Sets and Feature Groups all involve, for each concept, identifying the Feature Sets that are tagged with the concept and filtering these Feature Sets to remove certain Features Sets that are less relevant to the concept or might skew the results. These operations may be performed for each concept, with the desired feature, Feature Set and/or Feature Group scoring then performed as shown in blocks 309 and 311, 409 and 411, and 509 and 511.

As described above, in certain embodiments, the methods involve filtering the Feature Sets that are tagged with a particular concept to exclude certain Feature Sets. For example, for concepts relating to an organ such as liver, it may be desired to exclude Feature Sets tagged with hepatitis and include only Feature Sets relating to healthy or normal liver tissue. According to various embodiments, the Feature Sets may be filtered based on one or more of the following:

Exclusion of Feature Sets having tags in a particular taxonomy (e.g., excluding all Feature Sets tagged with a Disease from contributing to the concept score of an organ or tissue).

Exclusion of Feature Sets having tags in a particular branch of a given taxonomy or a specific combination of tags Exclusion of certain categories from categorization logic, e.g., because they are too general. For example, a concept such as "Disease" is not particularly useful. A "black list" of such concepts that should not show up in the results may be generated and used to filter out categories.

As described above, in certain embodiments, top level categories include all or some of the following: Diseases, Treatments and Tissues/Organs. An individual Feature Set may have tags from any or all of these categories. As an example, Feature Sets having the following tag combinations may be filtered according to the following logic:

| Tag Combinations | Data Category | | |
|---|---|---|---|
| | Diseases | Tissues/Organs | Treatments |
| Diseases | Yes | No | No |
| Diseases + Treatments | Yes | No | Yes |
| Diseases + Tissues | Yes | No | No |
| Diseases + Tissues + Treatments | Yes | No | Yes |
| Tissues | No | Yes | No |
| Tissues + Treatments | No | No | Yes |
| Treatments | No | No | Yes |

The above logic excludes Feature Sets that have tags categorized as either "Disease" or "Treatment" from contributing to the concept score of a tissue/organ. As discussed above, this is so that Feature Sets relating to diseases and/or treatments of these organs do not contribute to the concept score.

The decision logic may be based on the type of experimental data/model under consideration. As noted above, experiments done in cell lines may have little to do with the original disease tissue source for the cell line. Thus, a cell line Feature Set tagged with the original disease concept may skew the statistics with effects unrelated to the disease if allowed to contribute to the concept score of that disease. For example, if there are several hundred biosets (Feature Set) associated with MCF7 breast cancer cells treated with various types of compounds, without filtering these out, there be a significant "bias" when scores are computed for the concept "breast cancer." In this case, filtering the Feature Sets may require excluding certain branches of a taxonomy when a particular disease concepts are scored.

3. Queries

The description herein of methods, computational systems, and user interfaces for creating and defining a Knowledge Base provides a framework for describing an advanced categorization querying methodology that may be employed with the present invention. The querying methodology described herein is not however limited to the specific architecture or content of the Knowledge Base presented above. Generally, a query involves designating specific content to generate a query result in which the concepts most relevant to the designated content are provided. In certain embodiments, these concepts are grouped by category (e.g., Disease, Treatment, Tissue, Biogroup, Gene, etc.) so that the most relevant concepts for the designated content in each category are shown. The advance categorization or concept querying may be used in conjunction with or apart from the querying methodology described in U.S. Patent Publication 20070162411, in which specific content is designated to be compared against other content in a field of search.

Figure 6A:
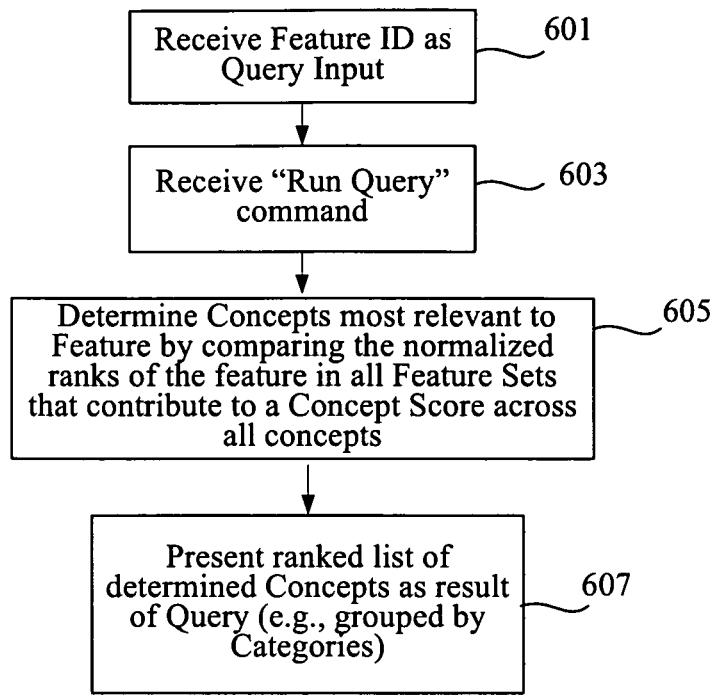
FIG. 6A is a process flow diagram depicting some operations in a query identifying a feature in accordance with certain embodiments.

As examples, the following discussion will focus on three general types of queries: features (e.g., genes), Feature Sets and Feature Groups. First, FIG. 6A shows an overview of a query identifying a feature. As illustrated, the process begins by receiving the identity of a feature input (block 601) followed by receiving a "Run Query" command (block 603). The query is run by determining the most relevant concepts to the feature by comparing the normalized ranks of the queried feature in all Feature Sets that contribute to a concept score across all (or at least a plurality of) concepts (block 605). As described above, concept scoring is based on determining the Feature Sets that contribute to a concept score (see, e.g., blocks 305 and 307 of FIG. 3). Comparing the normalized ranks across all concepts to compute a feature-concept score ($F_n$-$C_m$) according to certain embodiments is discussed above with respect to FIG. 3. Note that if the feature-concept scores are pre-computed as described above with respect to FIG. 3, running the query may involve sorting the pre-computed concept scores feature or otherwise obtaining the top scoring concepts for the queried feature. The next operation in the depicted query involves presenting to the user the ranked list of concepts (i.e., the query result). See block 607. As in other embodiments described herein, the resulting concepts may be conveniently displayed as grouped by category. For example, the results may show the top 10 concepts for each top-level category, and/or designated sub-category in an ontology.

FIG. 7 presents a screen shot of a user interface window 701 displaying results of a feature query. In this specific example, the Gata2 gene is queried as shown at 703. The results of the query are shown at 705: the most significant or relevant concepts as grouped by Tissues/Organs, Treatments and Diseases are listed in descending order of relevance. The results may be expanded by the user, e.g., by clicking on a concept, to show the Feature Sets that 1) contributed to the concept score and 2) contain the queried feature. (In certain embodiments, these Feature Sets may be displayed by study as discussed in U.S. Patent Publication 20070162411). The results may also be expanded to display more concepts for each category. The screen shot depicted also shows the results of a query comparing the gene to other content under the heading "Individual Study Results," as described in U.S. Patent Publication 20070162411. The results may be further expandable by selecting one of these Feature Sets to display the feature(s) that match the queried feature and their rank within the selected Feature Set.

Figure 6B:
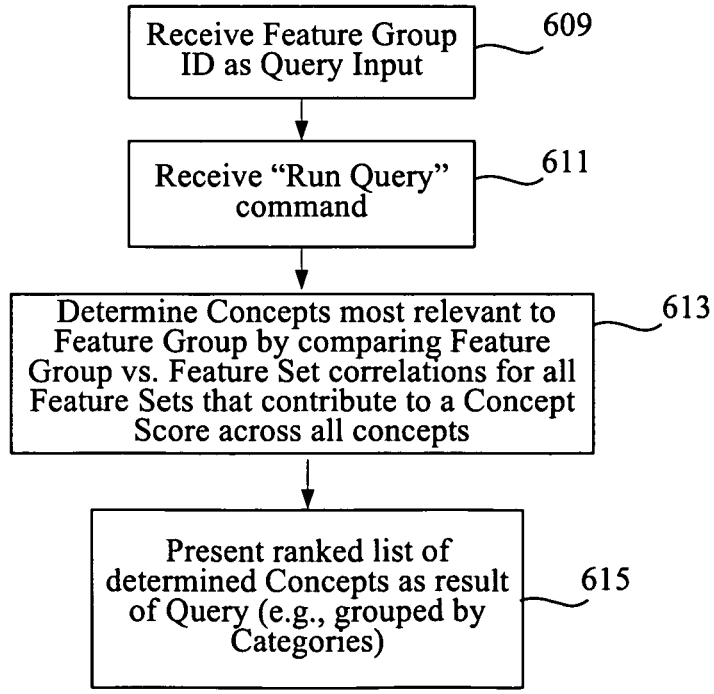
FIG. 6B is a process flow diagram depicting some operations in a query identifying a Feature Group in accordance with certain embodiments.

In certain embodiments, the results may also display, or be expanded to display sub-concepts that may be relevant. For example, a user clicking on a concept may expand the results to show a ranked list of child concepts of the clicked-on concept. Also, in certain embodiments, a list of Feature Sets that relevant to the concept may be displayed. These Feature Sets may be arranged by Study in certain embodiments. For example, with reference to FIG. 7, in certain embodiments, clicking or otherwise selecting a concept changes the list of studies in the bottom part of the page to a subset of the studies that are relevant to the concept. Thus, clicking on cancer will return studies related to lung cancer, breast cancer, etc., while selecting breast cancer would show the list of studies relevant to breast cancer. FIG. 6B shows an overview of a process of running a categorization or concept query on a Feature Group. Operations 609-615 are similar to the process described for a feature in FIG. 6A, except that running the query involves comparing the Feature Group v. Feature Set correlations for the queried Feature Group and all Feature Sets that contribute to a concept score. The comparison is typically done across all concepts. One implementation according to certain embodiments is discussed above with respect to FIG. 5. As with the features, if the Feature Group-concept scores are pre-computed, running the query may involve obtaining or receiving the scores from a pre-computed scoring table or matrix as shown at 118 in FIG. 1. FIG. 8 presents a screen shot of a user interface window 801 displaying results of a Feature Group query. In this specific example, the MAPK signaling pathway is queried. Significant concept results are presented by category at 805, as grouped by category and listed in descending order of significance.

Figure 6C:
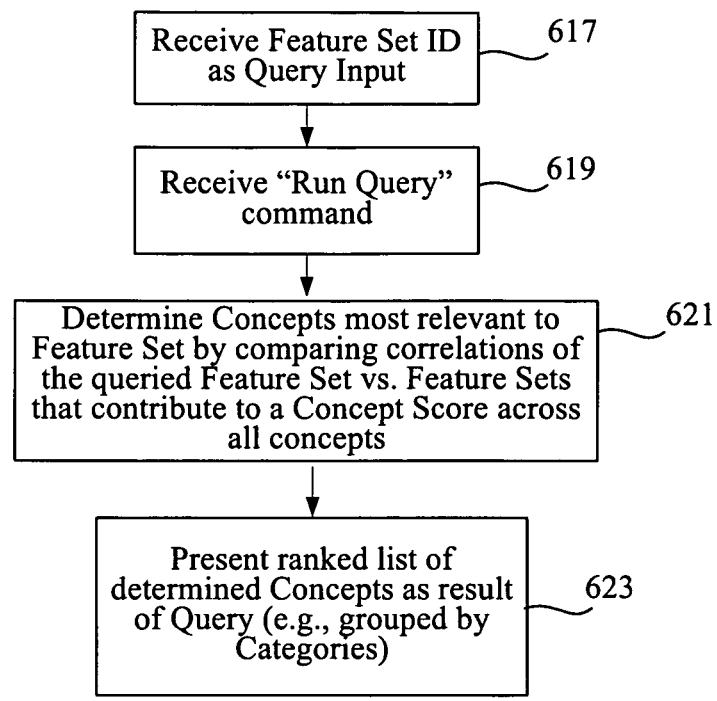
FIG. 6C is a process flow diagram depicting some operations in a query identifying a Feature Set in accordance with certain embodiments.

FIG. 6C shows an overview of a categorization query on a Feature Set. The process parallels that for a Feature Group, except the correlations of the queried Feature Set with the Feature Sets that contribute to a concept score compared across all concepts. See blocks 617-623. Also shown is a screen shot showing an example of results on a Feature Set query, in this specific example, the bioset Myc overexpression_CHGN vs. Control.

In certain embodiments, a query may identify multiple features, Feature Sets or Feature Groups. In these instances, the most significant concepts for the query as a group are found by averaging or otherwise factoring the concept scores for each of the features, Feature Sets or Feature Groups identified in the query.

Figure 10A:
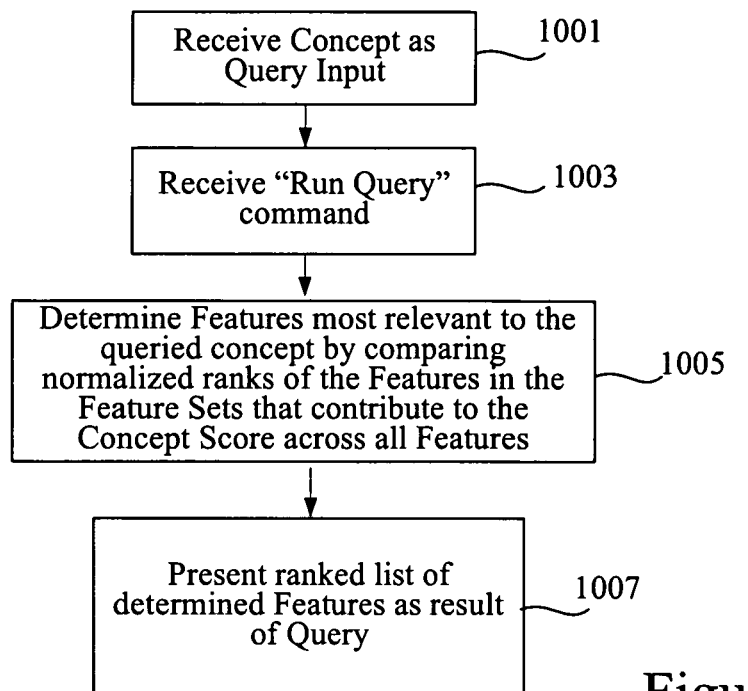
FIG. 10A is a process flow diagram depicting some operations in querying a concept to find the features most relevant the concept in accordance with certain embodiments.
Figure 10B:
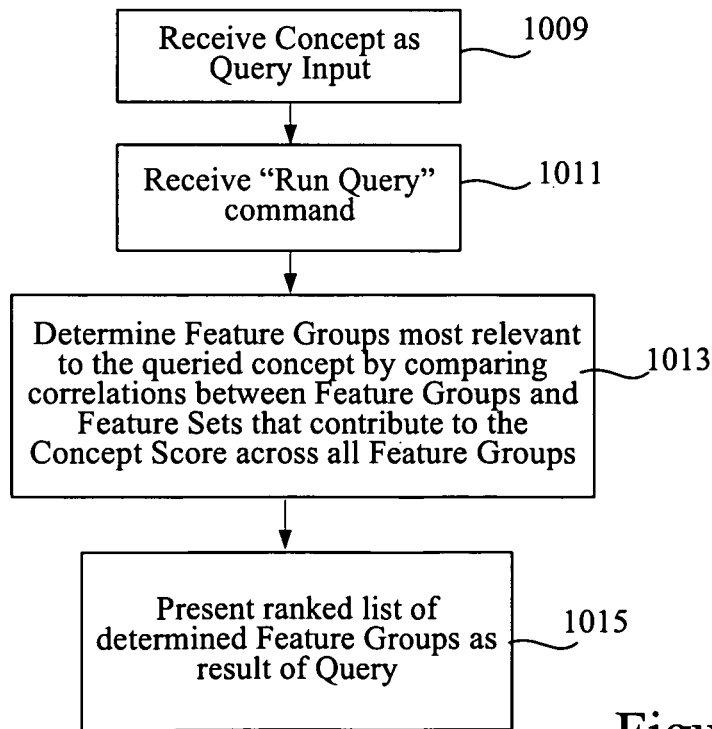
FIG. 10B is a process flow diagram depicting some operations in querying a concept to find the Feature Groups most relevant the concept in accordance with certain embodiments.

In certain embodiments, a query methodology for querying specific concepts against other content is provided. FIGS. 10a and 10b show methods of querying a concept to find the features and Feature Groups, respectively, most relevant to the concept. In FIG. 10a, a concept is received as a query input. See block 1001. A run query command is then received. See block 1003. A user may specify a query and give a run query command by entering a concept in a search box, clicking on a concept while browsing through a taxonomy, etc. Features most relevant to the queried concept are then determined by identifying the features in the Features Sets that contribute to the concept score and comparing the normalized ranks of the features in these Feature Sets across all features. See block 1005. As discussed above, the Feature Sets that contribute to the concept score are typically those Feature Sets that are tagged with the concept or one of its children and, in certain embodiments, also pass the category or other filters. Pre-computing the feature-concept score $F_n\text{-}C_m$ as described above provides a convenient way to quickly identify the most relevant features for a concept by sorting these scores to find the top scoring features. This is schematically depicted in FIG. 11, which shows a graphical depiction of a feature-concept scoring table such as that shown at 114 in FIG. 1. A ranked list of features is then presented to the user as a result of the query. See block 1007.

In FIG. 10b, Feature Groups most relevant to the queried concept are determined. Operations 1009-1015 parallel those in FIG. 10a. As discussed above with reference to FIG. 5, correlation or relevance between a concept and a Feature Group may be determined based on the correlation between a Feature Group and the Feature Sets tagged with the concept. Again, pre-computing Feature Group-concept score $FG_n\text{-}C_m$ provides a convenient way to find the top Feature Groups for a concept. FIG. 12 presents a screen shot of a user interface window 1201 displaying results of a concept query. In this specific example, rapamycin is queried. The most significant genes (features) and biogroups (Feature Groups) are listed at 1203 and 1205, respectively, in descending order of relevance.

Also in certain embodiments, concept-concept queries may be performed. For example, a user may identify a concept—by entering it in a search box, identifying it by browsing through a taxonomy, list of concepts, etc. A ranked list of concepts most significant to the query may be returned. In certain embodiments, to find related concepts for a concept all, or a subset of, the datasets (Feature Sets) that have been tagged by each of the concepts may be taken into consideration. The higher the overlap between these two sets—with the value normalized to factor in the number of datasets tagged with each of the concepts—the higher is the correlation between the two concepts. In this manner, concepts that are similar to a particular concept can be found.

In certain embodiments, concept-concept queries are performed by obtaining scores indicating the correlation between two concepts. These concept-concept scores may be computed by computing a summary or similarity function between all Feature Sets tagged with concept C1 (or its children) and Feature Sets tagged with concept C2 (or its children). In this manner, the correlation between each concept C1 and all other concepts may be obtained.

Figure 13:
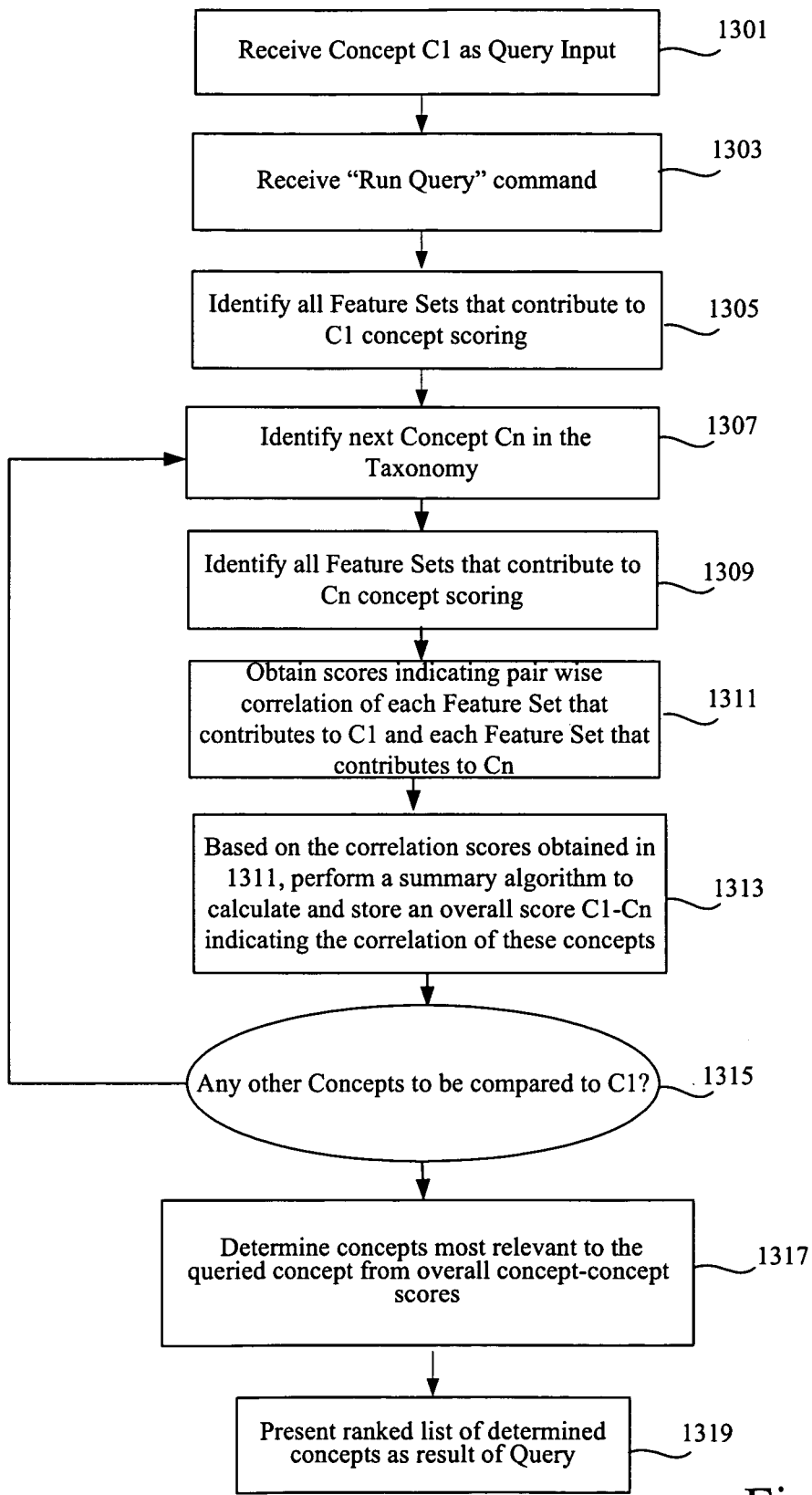
FIG. 13 is a process flow diagram depicting some operations in a query methodology for querying specific concepts against other concepts in accordance with certain embodiments.

FIG. 13 is a flow diagram illustrating operations in a query methodology for querying specific concepts against other concepts. The method begins in an operation 1301 in which a concept to be queried (C1 in the example in FIG. 13) is received. A command to run the query is received in an operation 1303. The Feature Sets that contribute to the concept score for C1 are identified as described above, e.g., by identifying all Feature Sets that are tagged with the concept or its children and in certain embodiments, filtering those Feature Sets to remove less relevant ones. See block 1305. A "next" concept Cn is then identified. See block 1307. According to various embodiments, concept-concept scores indicating the significance of every concept to C1 may be computed, or there may be a subset of concepts for which C1 is queried against, e.g., the subset may be a certain taxonomy or branch thereof. For example, a disease concept may be queried only against treatment concepts. If the field of search is more limited than all concepts, this may be performed automatically based on a certain protocol and/or may be indicated via a user input. All Feature Sets that contribute to concept Cn scoring are then identified as described above. See block 1309. Correlation scores indicating the pair-wise correlation of each Feature Set that contributes to C1 with each Feature Set that contributes to Cn are obtained. See block 1311. As discussed above, these correlation scores may be computed as discussed in U.S. Patent Publication 20070162411, or retrieved from a Scoring Table as depicted at 108 in FIG. 1. A summary or similarity function is then applied to these scores to produce an overall score C1-Cn indicating the correlation between these concepts. See block 1313. In an example, three biosets (Feature Sets) are tagged with C1: BS1, BS2 and BS3 and three biosets are tagged with C2: BS4, BS5 and BS6.

| Feature sets tagged with C1: | Feature sets tagged with C2: |
|---|---|
| BS1 | BS4 |
| BS2 | BS5 |
| BS3 | BS6 |

There are a total of nine scores representing pair-wise correlations between feature sets in C1 and C2 (BS1-BS4, BS1-BS5, BS1-BS6, BS2-BS4, etc.) To compute the correlation score between C1 and C2, a specialized summary function for all scores between all feature sets in C1 and all feature sets in C2 is applied to these nine scores. In performing the summary functions, attributes that may be included include one or more of Feature Sets that produce "positive scores" and total Feature Sets tagged with each concept. Furthermore, the same "exclusion filter" can apply here for any Feature Set tagged with a particular concept, i.e., in embodiments where the Feature Sets are filtered, the Feature Sets BS1, B2, etc. are the ones that passed the filter in addition to being tagged with the relevant concept.

Returning to FIG. 13, once a score indicating the correlation between C1 and Cn is calculated, there is a check for other concepts to be compared to or scored with C1. See block 1315. If there are, operations indicated at 1307-1315 are repeated. If not, the concepts most highly correlated to are determined from all of the concept-concepts scores calculated. See block 1317. A ranked list of concepts is then presented to the user as a result of the query. See block 1319.

Various operations described in FIG. 13 may be performed outside of a user query. For example, although FIG. 13 shows the concept-concept scores calculated in response to a user query, these scores may also be pre-computed in the same fashion as described above for feature-concept scoring, etc. A concept scoring table such as that represented in FIG. 1 may also include concept-concept scores. In certain embodiments, concept-concept correlation scoring may involve computing the correlation of each concept with all or a subset of all other concepts, while querying may involve a smaller subset of these concepts.

4. Data Source Information

Another aspect of the invention relates to using data source information to query and navigate knowledge in the Knowledge Base. Data source information may be divided into data source groups, with each group containing information about a particular aspect or aspects of the data source, including quality. According to various embodiments, data source information includes information relating to organism the data was derived from (e.g., gene expression in human cell lines, mouse cell lines exposed to a particular compound, etc.), data type (e.g., gene expression, proteinomics, diagnostic, therapeutic, etc.) and data authority level (e.g., experimental, high confidence, validated.)

Each Feature Set is typically associated with a single organism, though there may be instances in which it is associated with multiple organisms. The set of possible organism associations may include all known organisms as well one or more synthetic associations.

Each Feature Set may be associated with one or more data types, though typically a Feature Set is associated with a singe data type, e.g., gene expression, DNA mutation, SNP association, etc.

Data type information may include information about what was measured by the experiment (e.g., gene expression) as well as other information about that characterizes the data such as diagnostic or therapeutic. It may further include information about where the experimental data was reported or obtained (e.g., literature, clinical tests, etc.) or information about the quality or reputation of the source. A non-inclusive list of data types follows: diagnostic, therapeutic, phenotypic, genotyping, DNA mutation, gene expression, DNA methylation, Protein-DNA Binding (ChIP), proteomics, clinical trial and literature. Note that all of these data types may be included and presented to user together or may be separated into different data source groups (e.g., measured quantity in one group, diagnostic vs. therapeutic in another group, etc.).

Authority level refers to the extent the data has been validated. There are at least two authority levels, e.g., validated and non-validated. In certain embodiments, there are three authority levels: experimental, high confidence and validated, which in a particular embodiment is characterized by the following:
- validated: validated refers to the high level of validation, including results or data that are accepted in clinical practice, or by authorities such as the Food and Drug Administration, e.g., mutation data from the cancer census, gene target data from a drug bank
- high confidence: high confidence may include data or results observed in phenotypes (e.g., mice knockout data), that is well known (e.g., a known association between a gene mutation and a disease), or that agrees with a large number of other studies
- experimental: experimental data is the default association for data or results that do not meet the requirements for high confidence or validated. Typically data from individual experiments (e.g., individual gene expression) have an authority level of experimental.

In certain embodiments, Feature Sets in the Knowledge Base are labeled with data source information labels, for example, in one embodiment, each Feature Set may have an organism label, a data source label and an authority label as part of a standardized format for importation into the Knowledge Base. As is discussed further below, these labels may be used to further filter query results to dynamically navigate through the Knowledge Base.

Figure 14B:
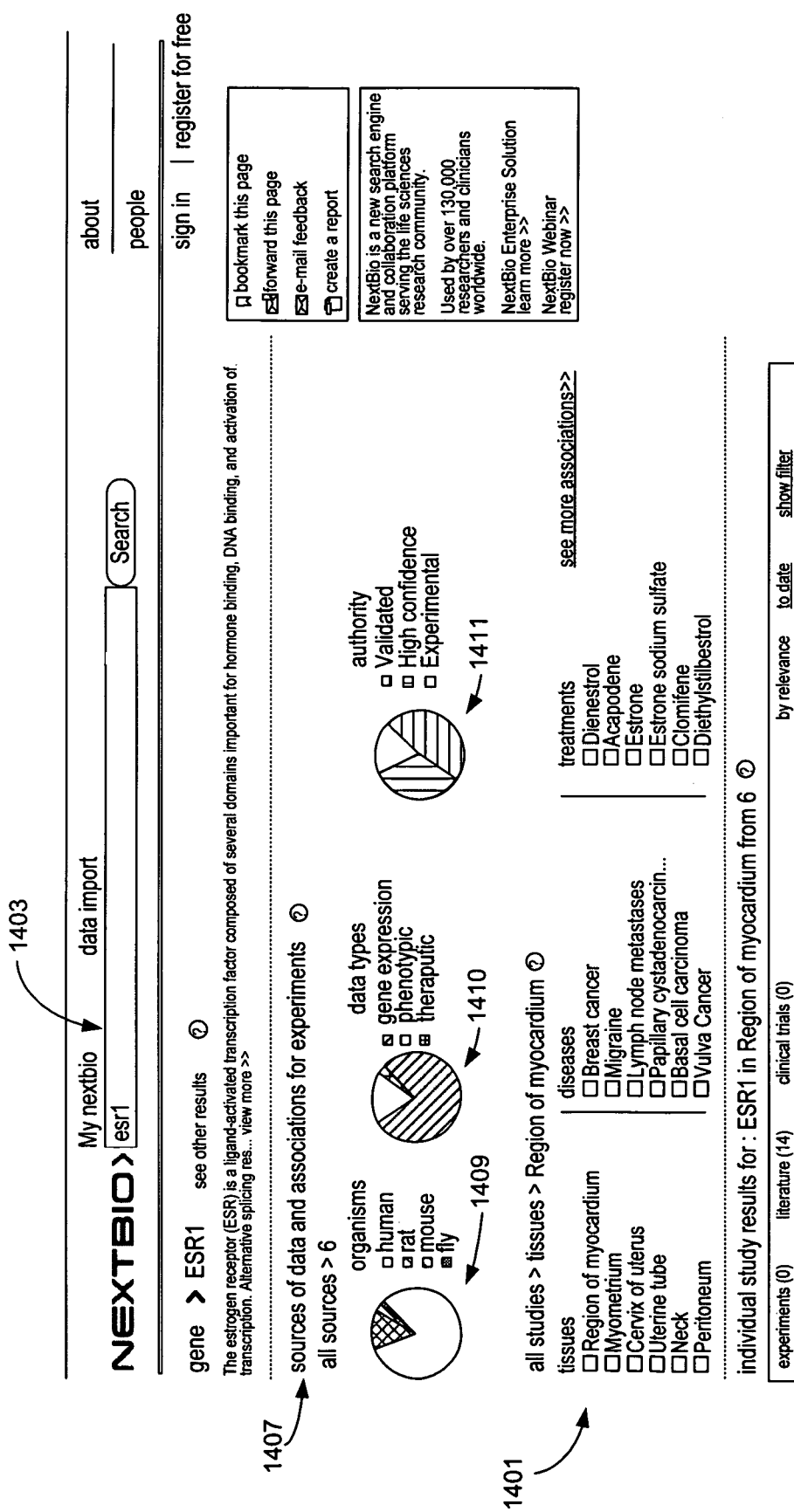
FIG. 14B is a screen shot of a user interface window displaying results of the feature query shown in FIG. 14A as filtered by the organism "human."
Figure 14C:
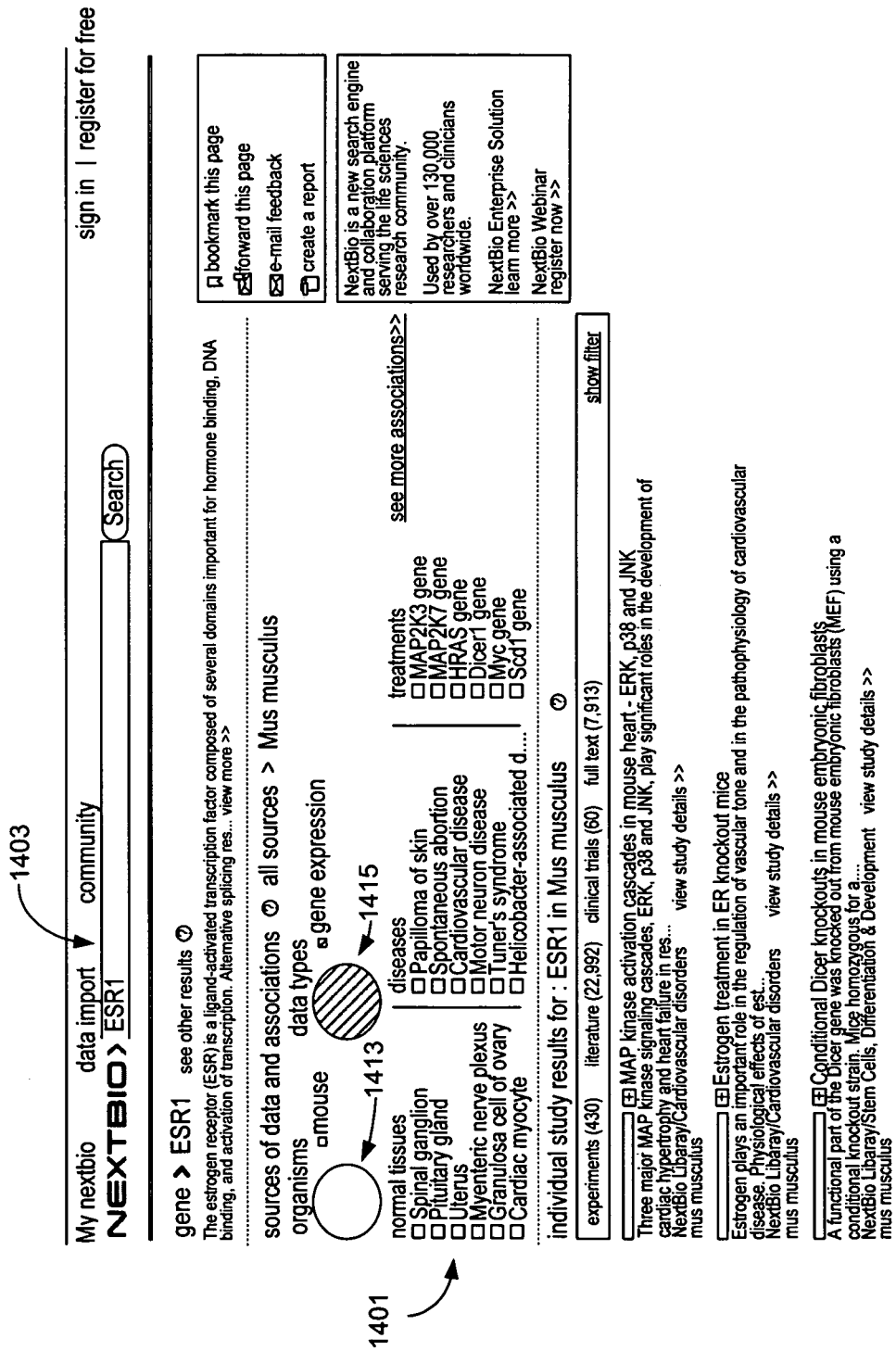
FIG. 14C is a screen shot of user interface window displaying the results of the query shown in FIG. 14A, as filtered by the organism "mouse" and the data type "gene expression."

Information about the breakdown of the experimental data in the individual study results by data source may be presented to a user. FIG. 14A-14C presents screen shots illustrating how data source information may be used to display and navigate results of a query. In FIG. 14A, user interface window 1401 displays results of a feature query. In this specific example, the ESR1 gene is queried as shown at 1403. Concepts results are shown at 1405, with the color intensity of the square next to each concept indicating its significance to the top-ranked concept. In addition to the concept results shown at 1405, pie charts graphically depicting data source information for the query as shown at 1407. At 1409, for example, a pie chart depicting Feature Sets contributing to the query result as divided by organism is displayed. In the example shown in FIG. 14A, the pie chart 1409 shows that data from human, mouse and rat contributes to the results for the ESR1 query. Similarly, pie chart 1410 shows gene expression, phenotypic and therapeutic data sources. In the example shown in FIG. 14B, the pie chart 1409 shows that most of the Feature Sets in the query results are from human sources, with rat, worm and fly data also present. Similarly, data type information is displayed at 1410. The pie chart 1410 shows that gene expression data is the largest data type, with genotyping (SNP) and proteomics data also contributing. At 1411, a pie chart displaying the breakdown by authority level of the query results for ESR1 is shown.

These results may be navigated by selecting one or more of the data sources to filter the results. FIG. 14C is a screen shot of user interface window 1401 displaying the results of the query shown in FIG. 14A, filtered by mouse and gene expression. Pie charts 1413 and 1415 show only that data sources associated with mouse and gene expression, respectively, are included in the results. Filtering by mouse and gene expression updates all results: the data source results are updated as are the most significant concepts and the individual study results. For example, if a user filters by mouse only, the pie chart 1415 shows the breakdown of data source types associated with all the mouse-specific experimental data contributing to the results. Determining the category results for each data source-specific (e.g., organism-specific, data type-specific, or authority level-specific) filter is discussed below. Note that a user may navigate by filtering by one data source group, or as in FIG. 14C, by multiple groups.

In certain embodiments, a user may identify, e.g., by clicking on any source to filter the results to that source. Any concept may be identified the user, e.g., by clicking on it, to filter the experiments (e.g., as indicated by study results) and data sources for that concept.

A. Filtering by Organism or Data Type

Figure 15A:
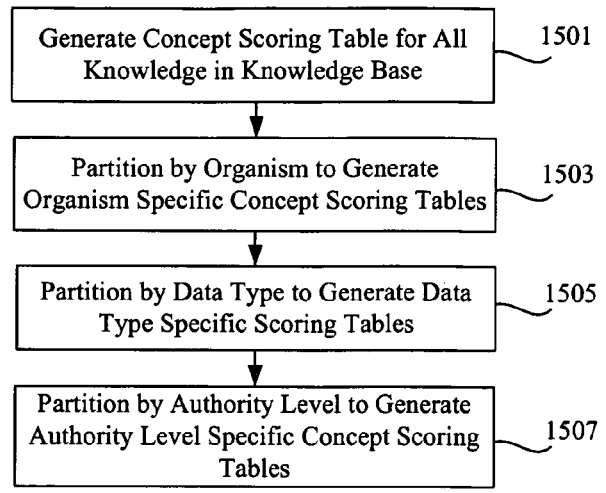
FIG. 15A is a process flow diagram depicting some operations of a method for determining the most relevance of concepts for feature, Feature Set and Feature Group queries according to certain embodiments.

According to various embodiments, filtering results by organism or data type involves recalculating the most relevant concepts for the particular feature, Feature Set or Feature Group query as filtered by the organism or the data type. This may be done during the preprocessing stage as discussed above with respect to FIGS. 3-5. A concept scoring table is generated as described with reference to FIGS. 3-5 for all knowledge in the Knowledge Base; individual Concept-feature; Concept-Feature Set and Concept-Feature Group tables are then partitioned by organism, data type or other data source information group. FIG. 15A is a process flow diagram representing operations of a method for determining the most relevance of concepts for feature, Feature Set and Feature Group queries according to certain embodiments. First, in an operation 1501, an unfiltered concept scoring table is generated, i.e., a scoring table for all data in the Knowledge Base. This may be done as explained above with reference to FIGS. 3-5, with a graphical representation of a concept scoring table shown at 112 in FIG. 1. In an operation 1503, the data is then partitioned on a per-organism basis to generate a scoring table for each organism. Methods of generating an organism-specific scoring table are discussed further below. In an operation 1505, the data is partitioned on a per-data type basis to generate a scoring table for each data type. Methods of generating organism-specific and data type-specific scoring tables are discussed further below. In an operation 1507, the data is partitioned on a per-authority level basis to generate a scoring table for each authority level. This is also discussed further below. While the method in FIG. 15A refers to organism, data type and authority level, the method may be performed using any data source information group described above in addition to or instead of these groups. Filtered concept-feature, concept-Feature Set and concept-Feature Group information may also be stored in any appropriate format.

Figure 15B:
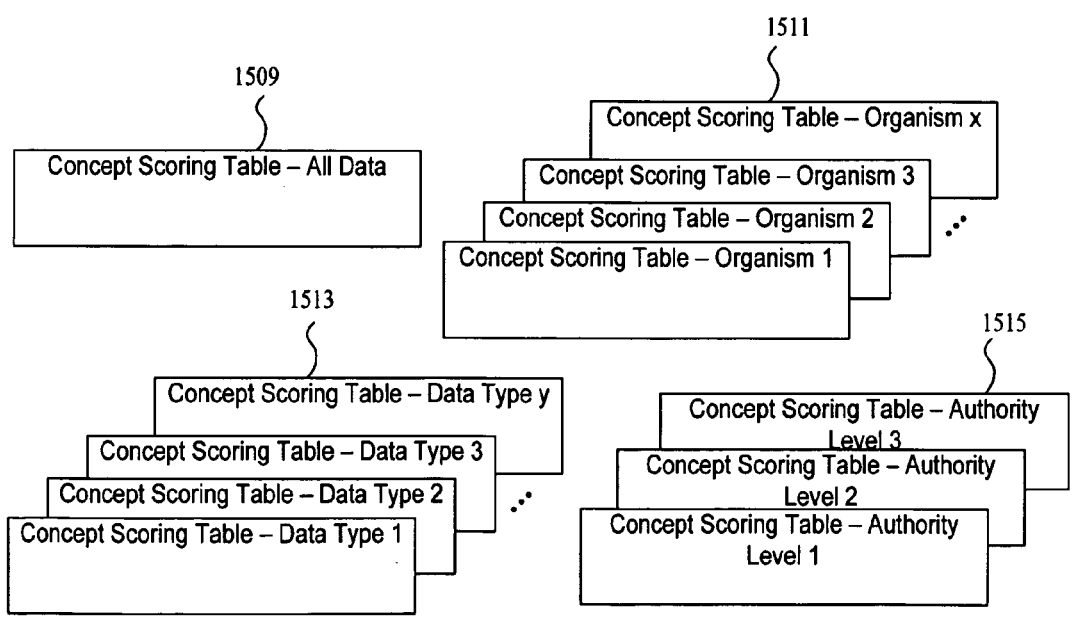
FIG. 15B shows a graphical representation of the resulting unfiltered and filtered concept relevance information in the form of concept scoring tables according to certain embodiments.

FIG. 15B shows a graphical representation of the resulting unfiltered and filtered concept relevance information in the form of concept scoring tables. At 1509, a concept scoring table for all data is depicted; this table contains concept relevance information for possible queries (e.g., feature, Feature Set and Feature Group) across all organisms, data types, authority levels and other data source groups. As shown at 112 in FIG. 1, in certain embodiments, the table contains information about the relevance of each concept to each feature, information about the relevance of concept to each Feature Set and information about the relevance of each concept to each Feature Group in the Knowledge Base. (As indicated above, in certain embodiments, there may only be a subset of features and/or taxonomy concepts for which a concept score is calculated and stored). At 1511, concept scoring tables as filtered by organism are depicted: a concept scoring table for each of m organisms, each containing concept-feature scores, concept-Feature Set scores and concept-Feature Group scores. Similarly, at 1513, concept scoring tables for each of n data types are depicted. At 1515, concept scoring tables for each authority level are depicted. (Three authority levels are depicted in the example shown in FIG. 15B, but there may be from two to any number of authority levels according to various embodiments).

Figure 16:
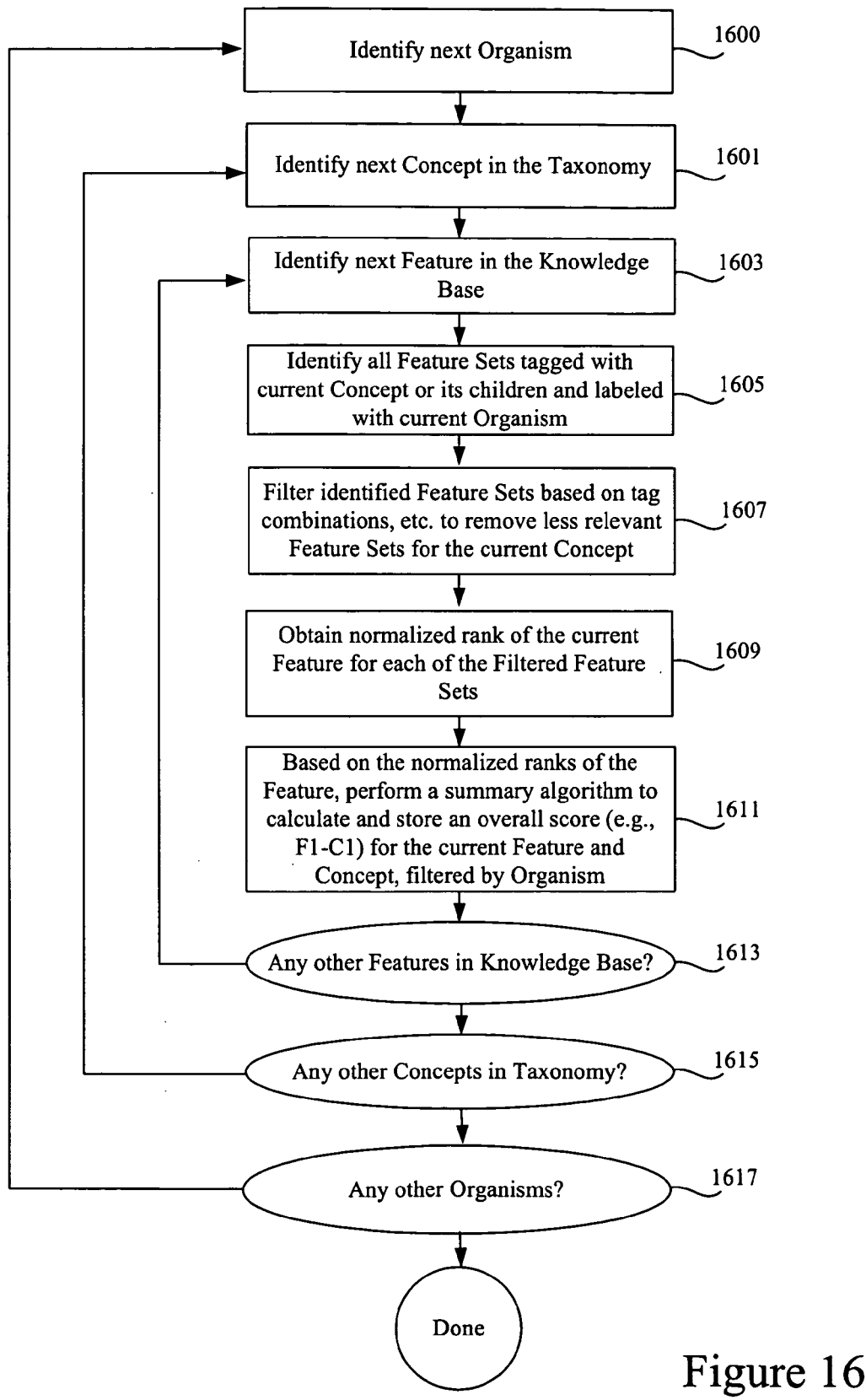
FIG. 16 is a process flow diagram depicting some operations of a method for determining concept-feature scores for each organism according to certain embodiments.

Calculating concept-feature, concept-Feature Set and concept-Feature Group scores for organisms and data types generally involves the same methodology employed for calculating the concept scoring table for all data, described above with respect to FIGS. 3-5, with only Feature Sets labeled with the organism, data type or other data source groups, considered. An example of determining concept-feature scores for each organism is depicted in FIG. 16.

As depicted, the process begins at an operation 1600 where the system identifies a "next" organism in the Knowledge Base. As described above, the set of all organisms may include all known actual and synthetic organisms. A concept and feature are set for the current iteration. See blocks 1601 and 1603. The process next identifies all Feature Sets that labeled with the current organism and that are tagged with 1) the current concept or 2) its' children concepts. See block 1605. The identified Feature Sets are filtered to remove (or in certain embodiments, reweight) Feature Sets that are less relevant to the concept or that would skew the results. See block 1607. The normalized rank of the current feature is obtained for each of the filtered Feature Sets, i.e., the Feature Sets remaining after removing the less relevant Feature Sets. See block 1609. After these ranks are obtained, an overall score $F_n$-$C_m$ indicating the relevance of the concept to the feature is obtained. See block 1611. The overall score $F_n$-$C_m$ is then stored, e.g., in an organism-specific concept scoring table (as shown in FIG. 15B) at 1611. Iteration over all features is controlled as indicated at decision block 1613, iteration over all concepts is controlled as indicated at decision block 1615, and iteration over all organisms is controlled (as the outer loop) as indicated at decision block 1617. As described, the process in FIG. 16 mirrors that of FIG. 3, with only Feature Sets that are tagged with the relevant concepts and labeled with the current organism considered. Similarly, the concept-Feature Set scoring may be performed described in FIG. 4, with only Feature Sets labeled with the current organism and tagged with the current concept or its children identified in operation 405. Concept-Feature Group scoring may be performed as described in FIG. 5, with only with only Feature Sets labeled with the current organism and tagged with the current concept or its children identified in operation 505. The organism-specific concept-feature, concept-Feature Set and concept-Feature Group scores are stored for later use, e.g., such as in the concept scoring tables represented in FIG. 15B, allowing efficient dynamic navigation through the query results. In the same manner, the data is partitioned by data type to determine the most relevant or significant concepts for each possible query as filtered by data type. Similarly, this approach may be used to partition data based on any data source group.

B. Filtering by Authority Level

As described above, filtering by organism, data type and other data source groups is performed based on the data source group labels associated with the Feature Sets. Filtering authority level may also be performed in this manner. However, in certain embodiments, filtering by authority level is based on corroboration within the Knowledge Base that a given concept is significant to a particular feature, Feature Set or Feature Group query. This allows the authority level assigned to a particular query to reflect the collective evidence of the Knowledge Base, and not just the authority level or levels assigned to the individual experiments. For example, an individual experiment may show a connection between a particular feature (e.g., a gene) and breast cancer, with the corresponding Feature Set labeled experimental. If there is enough corroboration in the Knowledge Base, however, of the gene being linked to breast cancer, then the gene in question may have a higher authority level than experimental for the concept "Breast Cancer."

Figure 17A:
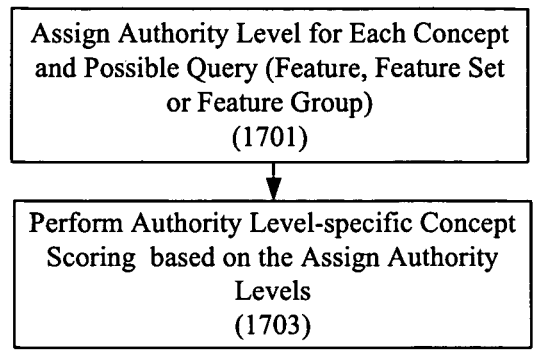
FIG. 17A is a process flow diagram depicting some operations of a method of employing authority levels according to various embodiments.

FIG. 17A is a process flow diagram showing operations in a method of employing authority levels according to various embodiments. First, a single authority level is assigned to each concept for each Feature, Feature Set and Feature Group relevant to that concept. See block 1701. For example, the concept "Breast Cancer" is assigned a single authority level (e.g., experimental, high confidence or validated) for the ESR1 gene, a single authority level for the RAP1A gene, etc. Similarly, the concept "Breast Cancer" is assigned a single authority level for the Feature Set "breast cancer basal-like CHGN vs. normal-like tumors," a single authority level for the Feature Set "breast cancer chemotherapy CHGN vs. non-treated patients," a single authority level for the Feature Group "Cell Cycle," a single authority level for the Feature Group "IGF-1 Pathway," etc. The assigned authority levels may then be used to perform concept scoring for each authority level, e.g., to populate concept scoring tables as shown at 1515 in FIG. 15B. See block 1703.

Figure 17B:
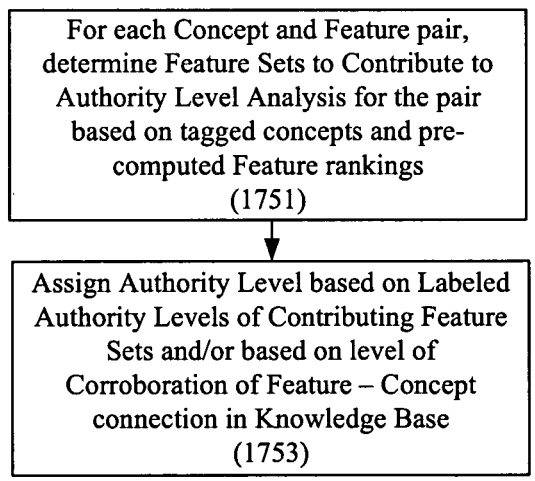
FIG. 17B shows a flow diagram depicting some operations in a method of assigning an authority level to a concept for a feature according to various embodiments.

FIG. 17B shows a flow diagram illustrating operations in a method of assigning an authority level to a concept for a feature. For each concept-feature pair, the Feature Sets that contribute to the authority level analysis are determined in an operation 1751. As discussed further below, the contributing Feature Sets are selected based on the tagged concepts of each Feature Set and the normalized ranks of the feature in the Feature Sets. An authority level is then assigned in an operation 1753 based on 1) the default (labeled) authority levels of each of the individual contributing Feature Sets and/or 2) the level of corroboration of the significance of that feature to the concept. Analogous methods may be used to assign authority levels to a concept for Feature Sets and Feature Groups, with the contributing Feature Sets chosen based on pre-computed Feature Set-Feature Set scores and pre-computed Feature Set-Feature Group scores, respectively.

Figure 18A:
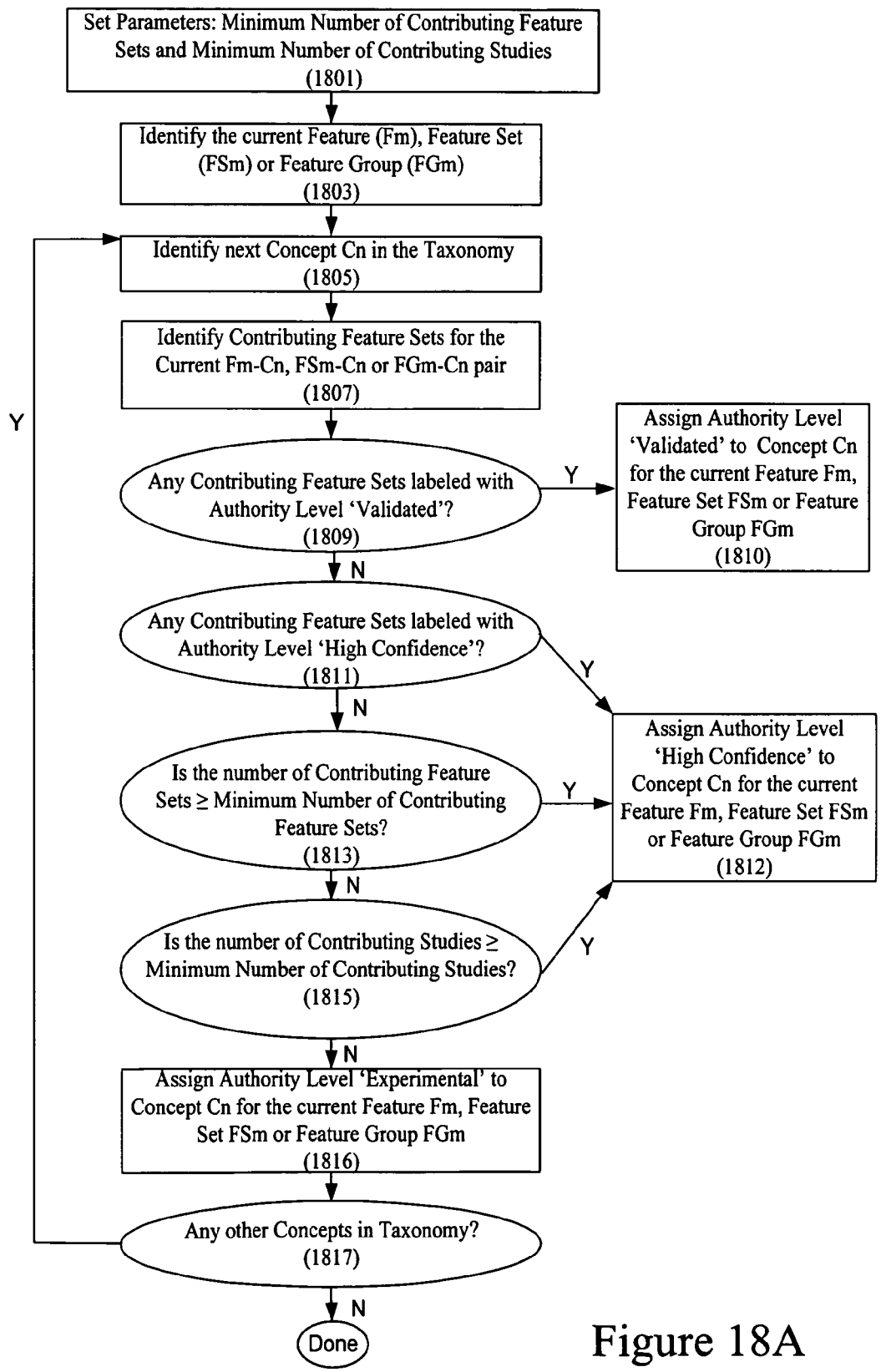
FIG. 18A shows an example of a process flow that may be employed to assign an authority level to a feature, Feature Set or Feature Group according to certain embodiments.

FIG. 18A shows an example of a process flow that may be employed to assign an authority level to a feature, Feature Set or Feature Group according to certain embodiments. As depicted the process begins at an operation 1801, in which two parameters are set: Minimum Number of Contributing Feature Sets and the Minimum Number of Contributing Studies. These parameters are chosen to identify the minimum amount of corroborating data in the Knowledge Base that supports assigning a concept a higher authority level for a particular feature, Feature Set or Feature Groups. (A contributing study is a study that contains a contributing Feature Set). The parameters chosen in operation 1801 may be constant for all concepts, features, Feature Sets and Feature Groups or may vary depending on the concept type, query type, etc. In certain embodiments, a user is able to assign default authority levels during data importation. The system contains reasonable default parameters, e.g., at least five related studies providing supporting evidence.

As is described further below, the parameters set in operation 1801 allow a higher authority level to be assigned to a concept if there is enough evidence in the Knowledge Base that the feature, Feature Set or Feature Group is significant to the concept as revealed either by the number of Feature Sets or studies that corroborate the significance. The process then identifies the current Feature (Fm), Feature Set (FSm) or Feature Group (FGm) in an operation 1803. The next concept Cn is then identified in an operation 1805. (The process may involve an appropriate iteration over all combinations of concepts and features, all combinations of concepts and Feature Sets and all combinations of concepts and Feature Groups, however, for simplicity only an iteration over all concepts is shown for the identified feature, etc.) At this point, a feature-concept (Fm-Cn), Feature Set-concept (FSm-Cn) or Feature Group-concept ($FG_n$-$C_m$) pair is identified. Contributing Feature Sets may include Feature Sets correlated highly to the feature, Feature Set or Feature Group in question and are tagged with the appropriate concept. Further description of identifying contributing Feature Sets is shown below with respect to FIGS. 19-21.

At decision block 1811, the system determines if any of the contributing Feature Sets are labeled with the highest authority level, in this example, 'Validated.' See block 1810. If there are, the concept is assigned to an authority level of 'Validated' for the current feature, Feature Set or Feature Group. If not, the system determines if any of the contributing Feature Sets are labeled with the next highest authority level, in this example, 'High Confidence,' at decision block 1811. If there are, the concept is assigned an authority level of 'High Confidence' for the current feature, Feature Set or Feature Group. See block 1812. If not, the system determines if the number of contributing Feature Sets is greater than or equal to the minimum parameter or the number of contributing studies is greater than or equal to the minimum parameter. See blocks 1813 and 1815. If either decision block 1813 or 1815 is answered in the affirmative, the concept is assigned an authority level of 'High Confidence' for the current feature, Feature Set or Feature Group. See block 1812. If not, the concept is assigned an authority level of 'Experimental' for the current feature, Feature Set or Feature Group. See block 1816. Iteration over the concepts for the feature, Feature Set or Feature Group in question is controlled by decision block 1817. Although FIG. 18A shows a process flow for assigning one of three authority levels, the process can be modified to assign two or more authority levels depending on the embodiment.

Ultimately, an authority level is assigned to every concept for every feature, Feature Set and Feature Group that is relevant to the concept. This is represented schematically in FIG. 18B, which shows authority level (V, HC and E) assignments to each concept for each feature at 1851, authority level assignments to each concept for each Feature Set at 1853, authority level assignments to each concept for each Feature Group at 1855. (In instances where there is no data relevant to the particular concept and feature, Feature Set or Feature Group, i.e., there are no contributing Feature Sets, a null value is shown.)

Figure 19:
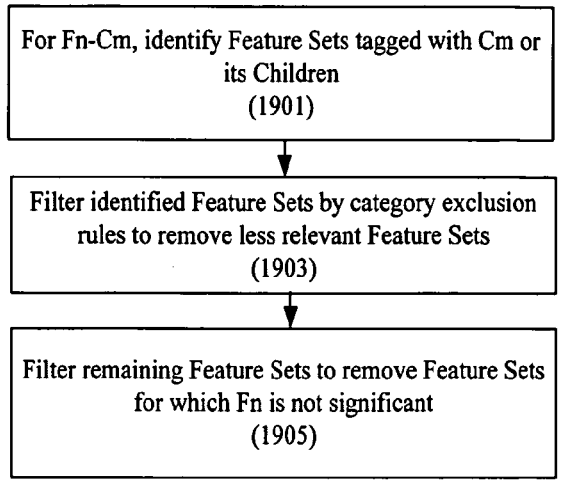
FIG. 19-21 are process flow diagrams depicting some operations in methods of determining contributing Feature Sets for an authority level analysis according to various embodiments.
Figure 20:
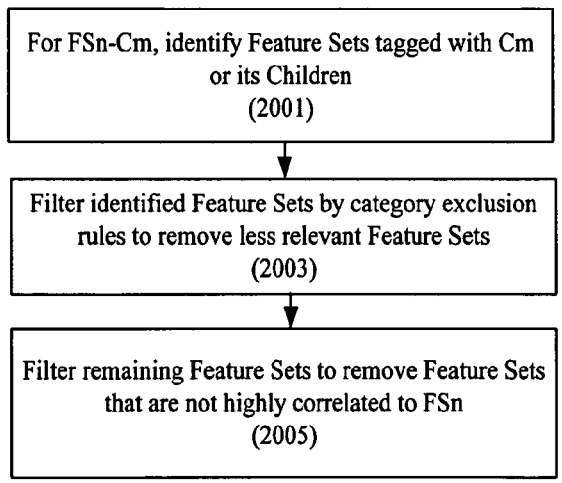
Figure 21:
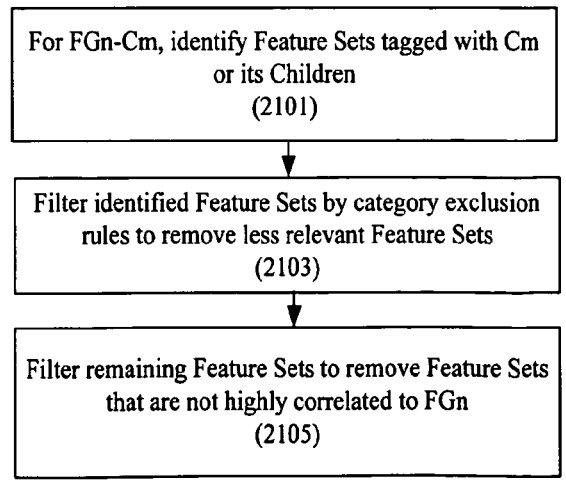

FIGS. 19-21 show process flows for implementing operation 1809, which determines contributing Feature Sets for the authority level analysis described above. As discussed above, the authority level analysis is used to identify if the collective evidence in the Knowledge Base that shows a particular concept is highly relevant to a particular feature, Feature Set or Feature Group; the contributing Feature Sets are Feature Sets that indicate a connection between the concept and the feature, Feature Set and Feature Group.

FIG. 19 describes a process flow for identifying contributing Feature Sets for features, FIG. 20 for Feature Sets and FIG. 21 for Feature Groups. FIG. 19 is a process flow to identify contributing Feature Sets for a feature and concept pair $F_n$-$C_m$. As shown, the process begins by identifying Feature Sets that are tagged with the concept or it children. See block 1901. In certain embodiments, the identified Feature Sets are then filtered according to concept category rules to remove less relevant Feature Sets in an operation 1903, e.g., using one or more of the exclusion rules described above with respect to concept scoring. The remaining Feature Sets are then filtered to remove Feature Sets for which the feature Fn is not significant in an operation 1905. In general, this involves setting a parameter that specifies the maximum normalized rank a feature must have within the Feature Set; if the normalized rank of Fn within the Feature Set is higher than this parameter, the Feature Set is removed from the group of contributing Feature Sets. FIGS. 20 and 21 show similar process flows for identifying contributing Feature Sets for Feature Set and Feature Group queries, respectively. As with determining contributing Feature Sets for feature queries, the processes for Feature Sets and Feature Groups begin with identifying Feature Sets that are tagged with the concept $C_m$ or its children. See blocks 2001 and 2101. Similarly, the Feature Sets may be filtered to remove less relevant Feature Sets or Feature Sets that may skew the results in operations 2003 and 2103, respectively. The remaining Feature Sets are then filtered to remove Feature Sets based on pre-computed Feature Set vs. Feature Set rank scores for the Feature Set queries (see block 2005 in FIG. 20) and on pre-computed Feature Set vs. Feature Group rank scores for Feature Group queries (see block 2105 in FIG. 21). As with feature queries, parameters setting minimum Feature Set vs. Feature Set rank scores and Feature Set vs. Feature Group rank scores may be set to determine which Feature Sets correlate highly enough to be considered a contributing Feature Set. In certain embodiments, a Feature Set may also be included if its rank score with the query Feature Set is among the top rank scores for all Feature Set vs. Feature Set scores for the query Feature Set, e.g., against all Feature Sets that satisfy the general category requirements applied in operation 2003. Contributing Feature Sets for a query Feature Group may also be applied determined in this manner. As an example, Feature Sets may be filtered according to the following logic (with the general category requirement column providing examples of filtering logic used in operations 1903, 2003 and 2103, and the filtering rule providing examples of filtering logic used in operations 1905, 2005 and 2105).

| | | Contributing Feature Set Requirement | |
|---|---|---|---|
| Query Type | Category Result Type | General Category | Filtering Rule |
| Feature | Tissue | Feature Set belong to Tissue | Feature Set should have the query gene with normalizedrank smaller than MAX_NORM_RANK |
| Feature | Disease | Feature Set belong to Disease and not belong to Treatment | |
| Feature | Treatment | Feature Set belong to Treatment | |
| Feature Set | Tissue | Feature Set belong to Tissue | Feature Set should have good rankscore with the query Feature Set: |
| Feature Set | Disease | Feature Set belong to Disease and not belong to Treatment | 1) rankscore > MIN_FEATURE SET_SCORE 2) rankscore is among top MIN_FEATURE SET_PERC percentage of all Feature Set- |
| Feature Set | Treatment | Feature Set belong to Treatment | Feature Set scores for the query Feature Set against all Feature Sets satisfying the general category requirement. |
| Feature Group | Tissue | Feature Set belong to Tissue | Feature Set should have good rankscore with the query biogroup: 1) rankscore > MIN_FEATURE GROUP_SCORE |
| Feature Group | Disease | Feature Set belong to Disease and not belong to Treatment | 2) rankscore is among top MIN_FEATURE GROUP_PERC percentage of all Feature Set- biogroup scores for the query |
| Feature Group | Treatment | Feature Set belong to Treatment | biogroup against all Feature Sets satisfying the general category requirement. |

Figure 22:
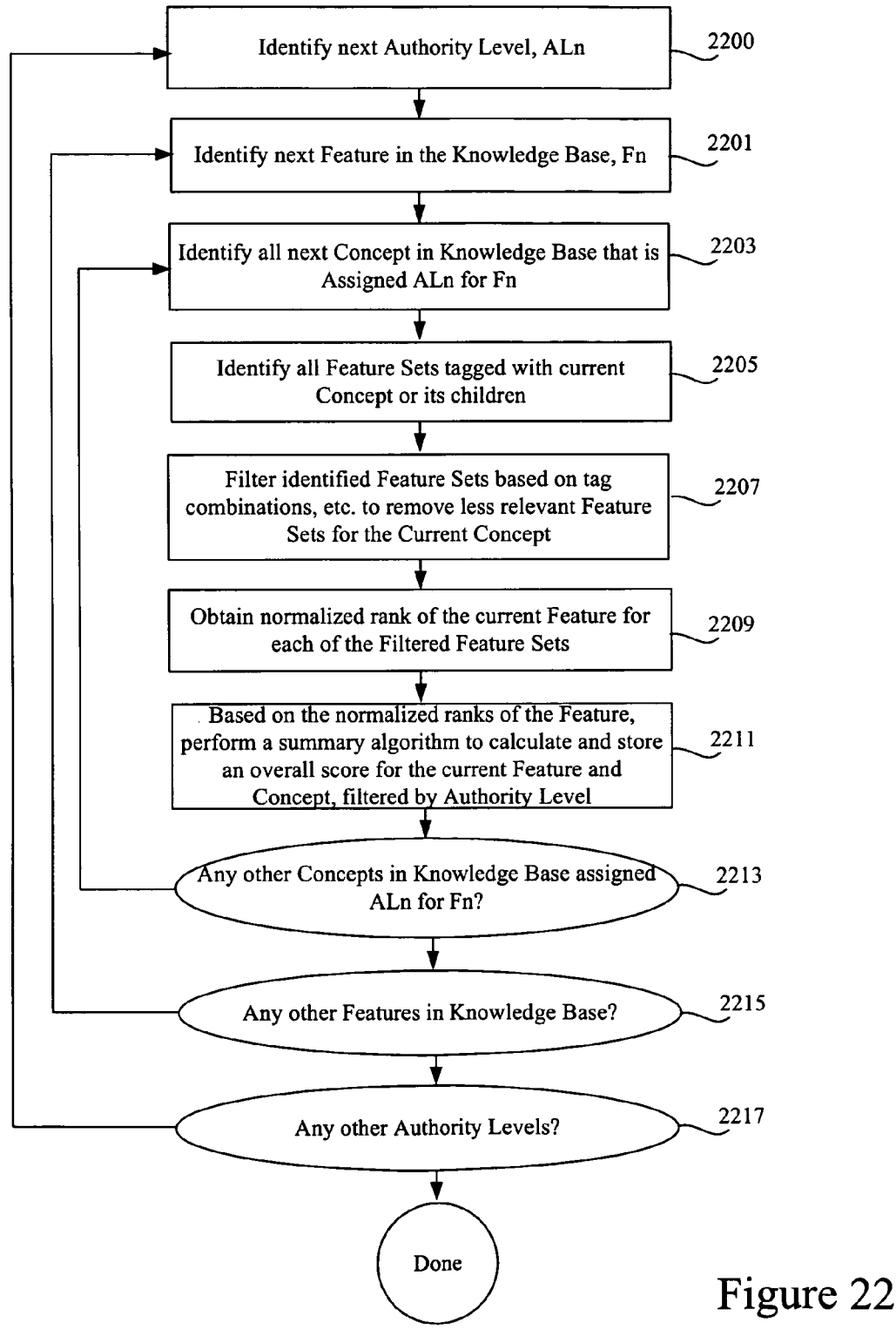
FIG. 22 is a process flow diagram depicting some operations of methods of concept-feature scoring for authority level filtering according to various embodiments.

Once assigned, the assigned authority levels may then be used to perform authority level-specific concept scoring. FIG. 22 shows a process flow for doing so for concept-feature scoring for authority level filtering. The process is similar to that described above in FIG. 3, using the assigned authority levels for individual feature-concept pairs. First in an operation 2200, the next authority level ALn (e.g., experimental, high confidence or validated) is identified. A next feature, Fn, is then identified in an operation 2201, with the process typically iterating over all features for the current authority level ALn. Assigned authority level information is then used to identify the next concept in the Knowledge Base that has an ALn assigned for the feature Fn in an operation 2203. In this manner, only feature-concepts pairs having the authority level in question are considered for the concept-feature scoring. Concept scoring then is performed as described in FIG. 3:

all Feature Sets tagged with the concept or its children are identified in an operation 2205; these Feature Sets are then optionally filtered, e.g., based on tag or category combinations in an operation 2207. In certain embodiments, operations 2205 and 2207 may make use of identifying and filtering operations performed during the authority level assignment described above with reference to FIG. 19. The normalized rank of the Fn for each of the filtered Feature Sets is then obtain in an operation 2209 to perform a summary algorithm to calculate an overall score for the current feature Fn and the current concept in an operation 2211. This is then stored, e.g., in one of the authority level concept scoring tables shown at 1515 in FIG. 15B. Iteration over all concepts that have an authority level ALn for the feature Fn is controlled by decision block 2213. Once all of the concepts having the current authority level for feature Fn are scored, iteration over all the features in the Knowledge Base is controlled by a decision block 2215. After all of the features have been scored, the concept scoring for that authority level is complete (e.g., the feature-concept sub-table of one of the concept scoring tables shown at 1515 is completely filled in). Iteration over the remaining authority levels is controlled by a decision block 2217. The process flows shown in FIGS. 4 and 5, for Feature Set-concept scoring and Feature Group-concept scoring, may be similarly modified to perform authority level-specific Feature Set-concept scoring and Feature Group-concept scoring.

For a concept query (e.g., of the types Tissue, Disease, or Treatment) the individual results under features or Feature Groups do not need to be computed. Instead, the authority level may be obtained from the one that is assigned to the reverse query. For example, for the query of the type Disease 'Breast Cancer', under its Gene categorization result, 'ESR1' will get the same authority level from the one that is computed for the query of the type Gene 'ESR1', under its Disease categorization result, 'Breast Cancer'.

Figure 23:
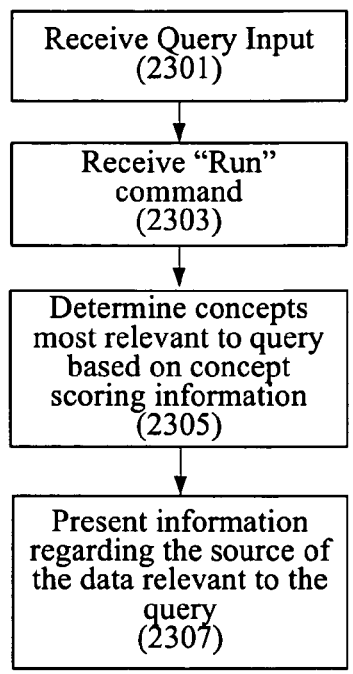
FIG. 23 is an example of a process flow that may be used to present data source information according to various embodiments.

The data source information may be employed with the querying methodology described above, to further present information regarding the data source in response to queries, including feature, Feature Set, Feature Group and concept queries. FIG. 23 is an example of a process flow that may be used to present data source information. First, a query input is received. See block 2301. Examples of query inputs include a feature, e.g., a gene, a Feature Set, a Feature Group or a concept. A run command is received in an operation 2303. In response to the query, the system determines the most relevant concepts to the query. See block 2305. (In other embodiments, the system may determine the most relevant features, Feature Sets or Feature Groups instead of or in addition to the most relevant concepts.) Information about the data sources of the results is then presented to the user, e.g., in the form of a pie chart organized by data source group or other format. See block 2307. This information may be determined in various manners, e.g., the number of Feature Sets or studies that contribute to a particular category.

Figure 24:
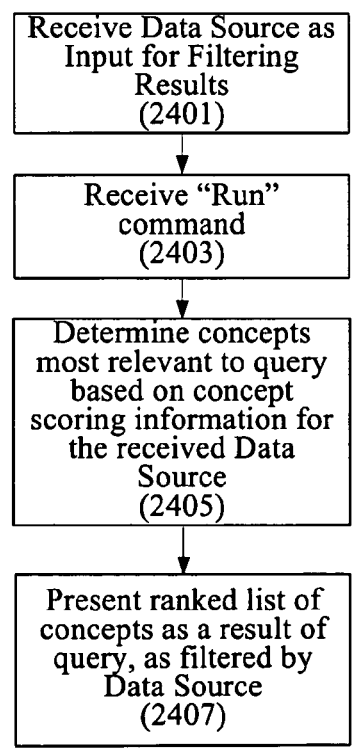
FIG. 24 is an example of a process flow for filtering data according to data source according to various embodiments.

Also as described above, methods of filtering data according to data source are also provided. FIG. 24 shows an example of a process flow. First, in an operation 2401, a particular data source is received as input to filter a query. A user may click on or select a type of organism (e.g., rat), data type (e.g., proteomics), authority level (e.g., validated), or other data source as described above with reference to FIG. 14A. Alternatively, a user may enter a data source, either before or after the initial query is run to filter the results of that query. A run command is received. See block 2403. The concepts most relevant to that query, as filtered by the data source, are then determined as described above with reference to FIGS. 6A-6C, 10a, 10b and 11, using the data source-specific concept scores generated as described above with reference to FIGS. 15-22. See block 2405. A ranked list of concepts is then presented to the user. See block 2407. Note that the data source information presented to the user also changes reflecting the filtered results.

In certain embodiments, a user may select more than one data source (e.g., two organisms, or one organism and a data type, etc.) to filter the results. In these instances, concept scoring information from each of the multiple data sources is used in a summary algorithm to find the most relevant concepts.

5. Example Embodiments

The methods, computational systems, and user interfaces described herein may be used with a wide variety of raw data sources and platforms. For example, microarray platforms including RNA and miRNA expression, SNP genotyping, protein expression, protein-DNA interaction and methylation data and amplification/deletion of chromosomal regions platforms may be used in the methods described herein. Microarray generally include hundreds or thousands of different capture agents, including DNA oligonucleotides, miRNAs, proteins, chemical compounds etc., arrayed by affixation to a substrate, localization in nanowells, etc. to assay an analyte solution. Platforms include arrays of DNA oligonucleotides, miRNA (MMChips), antibodies, peptides, aptamers, cell-interacting materials including lipids, antibodies and proteins, chemical compounds, tissues, etc. Further examples of raw data sources include quantitative polymerase chain reaction (QPCR) gene expression platforms, identified novel genetic variants, copy-number variation (CNV) detection platforms, detecting chromosomal aberrations (amplifications/deletions) and whole genome sequencing. QPCR platforms typically include a thermocycler in which nucleotide template, polymerase and other reagents are cycled to amplify DNA or RNA, which is then quantified. Copy number variation can be discovered by techniques including fluorescent in situ hybridization, comparative genomic hybridization, array comparative genomic hybridization, and large-scale SNP genotyping. For example, fluorescent probes and fluorescent microscopes may be employed to detect the presence or absence of specific DNA sequences on chromosomes.

In certain embodiments, high-content and high throughput compound screening data including screening compound effects on cells, screening compound effects on animal tissues and screening interaction between compounds, DNA and proteins, is used in accordance with the methods and systems described herein. High throughput screening uses robots, liquid handling devices and automated processes to conduct millions of biochemical, genetic or pharmacological tests. In certain HTS screenings, compounds in wells on a microtitre plate are filled with an analyte, such as a protein, cells or an embryo. After an incubation periods, measurements are taken across the plates wells to determine the differential impact of the compound on the analyte. The resulting measurements may then be formed into Feature Sets for importation and use in the Knowledge Base. High content screening may use automated digital microscopes in combination with flow cytometers and computer systems to acquire image information and analyze it.

The methods, computational systems, and user interfaces described herein may be used in a variety of research, drug development, pre-clinical and clinical research applications. For example, by querying a concept such as a disease, highly relevant genes and biological pathways may be displayed. Such genes or pathways may in turn be queried against compounds to find possible drug treatment candidates. Without the methods and systems described herein, these research paths are unavailable. Much more complex progressions and connections are enabled as well. Non-limiting examples of such applications include identifying genes linked to a disease, pathways linked to a disease and environmental effects linked to a disease, understanding mechanisms of development and disease progression, studying species diversity and cross-species comparison, identifying novel drug targets, identifying disease and treatment response biomarkers, identifying alternative indications for existing compounds, predicting drug toxicity, identifying a drug's mechanism of action, and identifying amplification or deletion of chromosomal regions.

Additional examples of pre-clinical and clinical research enabled by the methods and systems described herein include absorption, distribution, metabolism and excretion (ADME)—predicting a patient's drug response and drug metabolism, patient stratification into disease categories, e.g., determining more precisely patient stratification a patient's disease stage, identifying early disease biomarkers to enable early disease detection and preventive medicine, and using a patient's genetic profile to estimate the likelihood of disease, drug response or other phenotype. For example, in certain embodiments, a clinician uses a microarray to obtain genetic profile information. The genetic profile information may be imported into the Knowledge Base as a Feature Set. The methods and systems further include instant correlation of that Feature Set to all of the other knowledge in the Knowledge Base, and querying for relevant concepts as described above. Query results may then be navigated and expanded, also as described above.

6. Computer Hardware

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines is shown and described below.

In addition, certain embodiments relate to computer readable media or computer program products that include program instructions and/or data (including data structures) for performing various computer-implemented operations associated with at least the following tasks: (1) obtaining raw data from instrumentation, databases (private or public (e.g., NCBI), and other sources, (2) curating raw data to provide Feature Sets, (3) importing Feature Sets and other data to a repository such as database or Knowledge Base, (4) mapping Features from imported data to pre-defined Feature references in an index, (5) generating a pre-defined feature index, (6) generating correlations or other scoring between Feature Sets and Feature Sets and between Feature Sets and Feature Groups, (7) creating Feature Groups, (8) generating concept scores or other measures of concepts relevant to features, Feature Sets and Feature Groups, (9) determining authority levels to be assigned to a concept for every feature, Feature Set and Feature Group that is relevant to the concept, (10) filtering by data source, organism, authority level or other category, (11) receiving queries from users (including, optionally, query input content and/or query field of search limitations), (12) running queries using features, Feature Groups, Feature Sets, Studies, concepts, taxonomy groups, and the like, and (13) presenting query results to a user (optionally in a manner allowing the user to navigate through related content perform related queries). The invention also pertains to computational apparatus executing instructions to perform any or all of these tasks. It also pertains to computational apparatus including computer readable media encoded with instructions for performing such tasks.

Further the invention pertains to useful data structures stored on computer readable media. Such data structures include, for example, Feature Sets, Feature Groups, taxonomy hierarchies, feature indexes, Score Tables, and any of the other logical data groupings presented herein. Certain embodiments also provide functionality (e.g., code and processes) for storing any of the results (e.g., query results) or data structures generated as described herein. Such results or data structures are typically stored, at least temporarily, on a computer readable medium such as those presented in the following discussion. The results or data structures may also be output in any of various manners such as displaying, printing, and the like.

Examples of displays suitable for interfacing with a user in accordance with the invention include but are not limited to cathode ray tube displays, liquid crystal displays, plasma displays, touch screen displays, video projection displays, light-emitting diode and organic light-emitting diode displays, surface-conduction electron-emitter displays and the like. Examples of printers include toner-based printers, liquid inkjet printers, solid ink printers, dye-sublimation printers as well as inkless printers such as thermal printers. Printing may be to a tangible medium such as paper or transparencies.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

Figure 9:
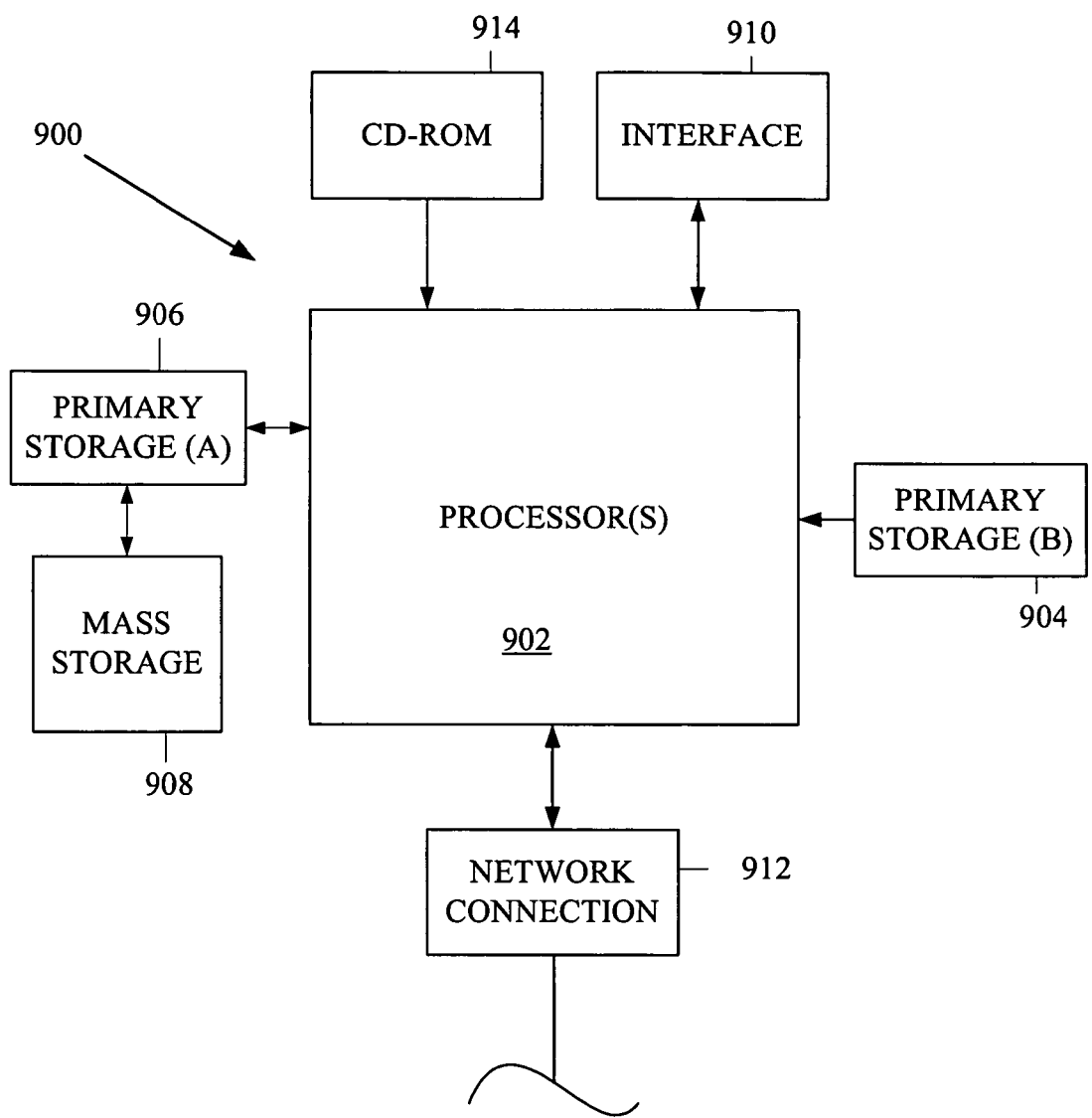
FIG. 9 is a diagrammatic representation of a computer system that can be used with the methods and apparatus described herein.

FIG. 9 illustrates, in simple block format, a typical computer system that, when appropriately configured or designed, can serve as a computational apparatus according to certain embodiments. The computer system 900 includes any number of processors 902 (also referred to as central processing units, or CPUs) that are coupled to storage devices including primary storage 906 (typically a random access memory, or RAM), primary storage 904 (typically a read only memory, or ROM). CPU 902 may be of various types including microcontrollers and microprocessors such as programmable devices (e.g., CPLDs and FPGAs) and non-programmable devices such as gate array ASICs or general-purpose microprocessors. In the depicted embodiment, primary storage 904 acts to transfer data and instructions uni-directionally to the CPU and primary storage 906 is used typically to transfer data and instructions in a bi-directional manner. Both of these primary storage devices may include any suitable computer-readable media such as those described above. A mass storage device 908 is also coupled bi-directionally to primary storage 906 and provides additional data storage capacity and may include any of the computer-readable media described above. Mass storage device 908 may be used to store programs, data and the like and is typically a secondary storage medium such as a hard disk. Frequently, such programs, data and the like are temporarily copied to primary memory 906 for execution on CPU 902. It will be appreciated that the information retained within the mass storage device 908, may, in appropriate cases, be incorporated in standard fashion as part of primary storage 904. A specific mass storage device such as a CD-ROM 914 may also pass data uni-directionally to the CPU or primary storage.

CPU 902 is also coupled to an interface 910 that connects to one or more input/output devices such as such as video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 902 optionally may be coupled to an external device such as a database or a computer or telecommunications network using an external connection as shown generally at 912. With such a connection, it is contemplated that the CPU might receive information from the network, or might output information to the network in the course of performing the method steps described herein.

In one embodiment, a system such as computer system 900 is used as a data import, data correlation, and querying system capable of performing some or all of the tasks described herein. System 900 may also serve as various other tools associated with Knowledge Bases and querying such as a data capture tool. Information and programs, including data files can be provided via a network connection 912 for access or downloading by a researcher. Alternatively, such information, programs and files can be provided to the researcher on a storage device.

In a specific embodiment, the computer system 900 is directly coupled to a data acquisition system such as a microarray or high-throughput screening system that captures data from samples. Data from such systems are provided via interface 910 for analysis by system 900. Alternatively, the data processed by system 900 are provided from a data storage source such as a database or other repository of relevant data. Once in apparatus 900, a memory device such as primary storage 906 or mass storage 908 buffers or stores, at least temporarily, relevant data. The memory may also store various routines and/or programs for importing, analyzing and presenting the data, including importing Feature Sets, correlating Feature Sets with one another and with Feature Groups, generating and running queries, etc.

In certain embodiments user terminals may include any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms. A server system in communication with a user terminal may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Although the foregoing invention has been described in some detail for purposes of clarity of understanding, it will be apparent that certain changes and modifications may be practiced within the scope of the invention. It should be noted that there are many alternative ways of implementing the processes and databases of the present invention. Accordingly, the present embodiments are to be considered as illustrative and not restrictive, and the invention is not to be limited to the details given herein.

The invention claimed is:

1. A computer implemented method for evaluating a correlation between (i) a gene, a SNP, a SNP pattern, a portion of gene, a region of a genome, or a compound, and (ii) a disease or a genotype, the method comprising:
    providing a taxonomy of categories of diseases and/or phenotypes arranged in a hierarchical structure comprising at least one top-level category;
    providing, a plurality of feature sets, each feature set comprising (a) two or more features, (b) associated experimentally-derived statistical information indicating one or more of: differential expression of said features, abundance of said features, responses of said features to a treatment or stimulus, and effects of said features on biological systems, and (c) a feature rank indicating the importance of the feature in an experiment from which the statistical information was derived,
    wherein
        the features are genes, SNPs, SNP patterns, portions of genes, regions of a genome, or compounds,
        at least some of the features have different names but correspond to a same gene, SNP, SNP pattern, portion of gene, region of a genome, or compound,
        the plurality of feature sets is obtained from across different experiments, platforms, and/or organisms, and
        at least some of said feature sets are associated with one or more categories in the taxonomy;
    providing a plurality of globally unique mapping identifiers;
    identifying, for each globally unique mapping identifier, one or more features associated with the globally unique mapping identifier;
    mapping, for each globally unique mapping identifier, the identified one or more features to the globally unique mapping identifier, thereby providing mapping data indicating mapping between a plurality of features and the plurality of globally unique mapping identifiers, wherein at least some features having different names but corresponding to a same gene, SNP, SNP pattern, portion of gene, region of a genome, or compound are mapped to a same globally unique mapping identifier;
    storing the mapping data in an index set;
    identifying, for each of a plurality of the categories in the taxonomy, contributing feature sets that contribute to scoring a category under consideration by identifying all feature sets among the provided feature sets that are associated with the category under consideration and its child categories in the taxonomy;
    combining the feature ranks of all features in the contributing feature sets that can be mapped to a globally unique mapping identifier under consideration based on the mapping data in the index set to obtain an overall score; and
    evaluating a correlation between (i) a gene, a SNP, a SNP pattern, a portion of gene, a region of a genome, or a compound corresponding to the globally unique mapping identifier under consideration, and (ii) a disease or a genotype corresponding to the category under consideration based on the obtained overall score.

2. The computer-implemented method of claim 1, wherein identifying contributing feature sets further comprises filtering, the identified contributing feature sets to remove at least some less relevant feature sets.

3. The computer-implemented method of claim 1, further comprising:
    for each of a plurality of categories in the taxonomy, receiving, feature set-feature set correlation scores between the contributing feature sets and a feature set obtained from a person; and
    combining the feature set-feature set correlation scores to obtain a category-feature set score indicating the relevance of the category under consideration to the feature set obtained from the person; and
    determining whether the person is likely to have the disease or the phenotype by comparing the category-feature set score to a criterion.

4. The computer-implemented method of claim 3, further comprising: administering, in response to determining that the person is likely to have the disease, the compound identified as the drug for the treatment of the disease.

5. The computer-implemented method of claim 1, further comprising:
    providing a plurality of feature groups each including a list of features related by a biological structure or function;
    for each of a plurality of categories in the taxonomy, receiving from one or more storage devices feature set-feature group correlation scores between the contributing feature sets and a plurality of the feature groups in the knowledge base;
    combining the feature set-feature group correlation scores to obtain category-feature group scores indicating the relevance of the category under consideration to each of a plurality of feature groups wherein each score provides an indication of the relevance of the category under consideration to the feature group under consideration; and
    determining whether the biological structure or function is likely linked to the disease or the phenotype by comparing the category-feature set score to a criterion.

6. The computer-implemented method of claim 5, wherein the biological structure or function comprises a biological pathway.

7. The computer-implemented method of claim 1, wherein retrieving feature ranks comprises receiving normalized ranks of the features in the contributing feature sets.

8. The computer-implemented method of claim 1, further comprising receiving feature set-feature set correlation scores from the one or more storage devices between the contributing feature sets and feature sets that contribute to the scoring of a plurality of the other categories in the knowledge base; and obtaining category-category scores based on the feature set-feature set correlation scores, the category-category scores indicating the relevance of the category under consideration to other categories in the taxonomy.

9. The computer-implemented method of claim 3, further comprising generating the feature set obtained from the person from raw data from a biological sample of the person, wherein the raw data includes information on one or more features with indications of one or more of: differential expression, abundance of said features, responses of said features to a treatment or stimulus, and effects of said features on biological systems.

10. The computer-implemented method of claim 9 further comprising importing the one or more generated feature sets into the knowledge base.

11. The computer-implemented method of claim 1 further comprising displaying to a user a list of categories relevant to identified information in the knowledge base.

12. The computer-implemented method of claim 1, wherein obtaining an overall score further comprises standardizing the feature ranks of the feature under consideration.

13. The computer-implemented method of claim 12, wherein standardizing the feature ranks of the feature under consideration includes using one or more of the following:
a normalized rank of the feature in each of the contributing feature sets for the category under consideration;
the total number of feature sets containing this feature that pass an inclusion criteria, and
the total number of contributing feature sets identified for the category under consideration.

14. The computer-implemented method of claim 1, wherein the identified one or more features and the globally unique mapping identifier are associated based on synonymy, a structural relation, a functional relation, a genomic coordinate, a chromosomal coordinate, and/or a sequence similarity.

15. A computer program product comprising one or more computer-readable non-transitory storage media having stored thereon computer executable instructions that, when executed by one or more processors of a computer system, cause the computer system to implement a method for evaluating a correlation between (i) a gene, a SNP, a SNP pattern, a portion of gene, a region of a genome, or a compound, and (ii) a disease or a genotype, the method comprising:
providing a taxonomy of categories of diseases and/or phenotypes arranged in a hierarchical structure comprising at least one top-level category;
providing, a plurality of feature sets, each feature set comprising (a) two or more features, (b) associated statistical information indicating one or more of: differential expression of said features, abundance of said features, responses of said features to a treatment or stimulus, and effects of said features on biological systems, and (c) a feature rank indicating the importance of the feature in an experiment from which the statistical information was derived,
wherein
the features are genes, SNPs, SNP patterns, portions of genes, regions of a genome, or compounds,
at least some of the features have different names but correspond to a same gene, SNP, SNP pattern, portion of gene, region of a genome, or compound,
the plurality of feature sets is obtained from across different experiments, platforms, and/or organisms, and
at least some of said feature sets are associated with one or more categories in the taxonomy;
providing a plurality of globally unique mapping identifiers;
identifying, for each globally unique mapping identifier, one or more features associated with the globally unique mapping identifier;
mapping, for each globally unique mapping identifier, the identified one or more features to the globally unique mapping identifier, thereby providing mapping data indicating mapping between a plurality of features and the plurality of globally unique mapping identifiers, wherein at least some features having different names but corresponding to a same gene, SNP, SNP pattern, portion of gene, region of a genome, or compound are mapped to a same globally unique mapping identifier;
storing the mapping data in an index set;
identifying, for each of a plurality of the categories in the taxonomy, contributing feature sets that contribute to scoring a category under consideration by identifying all feature sets among the provided feature sets that are associated with the category under consideration and/or its child categories in the taxonomy;
combining the feature ranks of all features in the contributing feature sets that can be mapped to a globally unique mapping identifier under consideration based on the mapping data in the index set to obtain an overall score; and
evaluating a correlation between (i) a gene, a SNP, a SNP pattern, a portion of gene, a region of a genome, or a compound corresponding to the globally unique mapping identifier under consideration, and (ii) a disease or a genotype corresponding to the category under consideration based on the obtained overall score.

16. A computer system comprising:
one or more processors; and
one or more storage devices in communication with the processors for storing a knowledge base and computer-executable instructions that, when executed by the one or more processors, cause the computer system to implement a method for evaluating a correlation between (i) a gene, a SNP, a SNP pattern, a portion of gene, a region of a genome, or a compound, and (ii) a disease or a genotype, the method comprising:
providing a taxonomy of categories of diseases and/or genotypes arranged in a hierarchical structure comprising at least one top-level category;
providing a plurality of feature sets, each feature set comprising (a) two or more features, (b) associated experimentally-derived statistical information indicating one or more of: differential expression of said features, abundance of said features, responses of said features to a treatment or stimulus, and effects of said features on biological systems, and (c) a feature rank indicating the importance of the feature in an experiment from which the statistical information was derived,
wherein
the features are genes, SNPs, SNP patterns, portions of genes, regions of a genome, or compounds,
at least some of the features have different names but correspond to a same gene, SNP, SNP pattern, portion of gene, region of a genome, or compound, the plurality of feature sets is obtained from across different experiments, platforms, and/or organisms, and at least some of said feature sets are associated with one or more categories in the taxonomy;

providing a plurality of globally unique mapping identifiers;

identifying, for each globally unique mapping identifier, one or more features associated with the globally unique mapping identifier;

mapping, for each globally unique mapping identifier, the identified one or more features to the globally unique mapping identifier, thereby providing mapping data indicating mapping between a plurality of features and the plurality of globally unique mapping identifiers, wherein at least some features having different names but corresponding to a same gene, SNP, SNP pattern, portion of gene, region of a genome, or compound are mapped to a same globally unique mapping identifier;

storing the mapping data in an index set;

identifying, for each of a plurality of the categories in the taxonomy, contributing feature sets that contribute to scoring a category under consideration by identifying all feature sets among the provided feature sets that are associated with the category under consideration and its child categories in the taxonomy;

combining the feature ranks of all features in the contributing feature sets that can be mapped to a globally unique mapping identifier under consideration based on the mapping data in the index set to obtain an overall; and evaluating a correlation between (i) a gene, a SNP, a SNP pattern, a portion of gene, a region of a genome, or a compound corresponding to the globally unique mapping identifier under consideration, and (ii) a disease or a genotype corresponding to the category under consideration based on the obtained overall score.

17. A computer implemented method for evaluating correlations between at least two items, each item is selected from a tissue, an organ, a disease, or a treatment, the method comprising:

providing a taxonomy of medical, biological and/or chemical categories arranged in a hierarchical structure comprising at least one top-level category comprising at least one of the group consisting of tissues or organs, diseases, and treatments;

providing a plurality of feature sets each comprising (a) two or more features, (b) associated experimentally-derived statistical information indicating one or more of: differential expression of said features, abundance of said features, responses of said features to a treatment or stimulus, and effects of said features on biological systems, and (c) a feature rank indicating the importance of the feature in an experiment from which the statistical information was derived, wherein the features are genes, SNPs, SNP patterns, portions of genes, regions of a genome, or compounds, at least some of the features have different names but correspond to a same gene, SNP, SNP pattern, portion of gene, region of a genome, or compound, the plurality of feature sets is obtained from across different experiments, platforms, and/or organisms, and at least some of said feature sets are associated with one or more categories in the taxonomy;

providing a plurality of globally unique mapping identifiers;

identifying, for each globally unique mapping identifier, one or more features associated with the globally unique mapping identifier;

mapping, for each globally unique mapping identifier, the identified one or more features to the globally unique mapping identifier, thereby providing mapping data indicating mapping between a plurality of features and the plurality of globally unique mapping identifiers, wherein at least some features having different names but corresponding to a same gene, SNP, SNP pattern, portion of gene, region of a genome, or compound are mapped to a same globally unique mapping identifier;

storing the mapping data in an index set;

identifying contributing feature sets that contribute to scoring a pair of categories under consideration by identifying all feature sets associated with the pair of categories under consideration and their child categories in the taxonomy;

obtain feature set-feature set correlation scores indicating pair-wise correlations between the contributing feature sets of one of the pair of categories under consideration and the contributing feature sets of the other of the pair of categories under consideration, wherein the pair-wise correlations are based on features that each can be mapped to a same globally unique mapping identifier across the pair of categories based on the mapping data in the index set;

calculating a category-category score based on the feature set-feature set correlation scores, the category-category score indicating the correlation between the categories in the pair based on the pair-wise correlation scores; and determining whether a tissue, an organ, a disease, or a treatment in a category in the pair is likely associated with a tissue, an organ, a disease, or a treatment in another category in the pair by comparing the category-category score to a criterion.

18. A computer implemented method for determining if a person is likely to have a disease or a phenotype, the method comprising:

providing a taxonomy of categories of diseases and/or phenotype arranged in a hierarchical structure comprising at least one top-level category;

providing a plurality of feature sets and/or feature groups, each feature set comprising (a) two or more features, (b) experimentally-derived associated statistical information indicating one or more of: differential expression of said features, abundance of said features, responses of said features to a treatment or stimulus, and effects of said features on biological systems, and (c) a feature rank indicating the importance of the feature in an experiment from which the statistical information was derived, and each feature group comprising a list of features related by biological or chemical structure or function, wherein the features are genes, SNPs, SNP patterns, portions of genes, regions of a genome, or compounds, at least some of the features have different names but correspond to a same gene, SNP, SNP pattern, portion of gene, region of a genome, or compound, the plurality of feature sets is obtained from across different experiments, platforms, and/or organisms, and at least some of said feature sets are associated with one or more categories in the taxonomy;

providing a plurality of globally unique mapping identifiers;

identifying, for each globally unique mapping identifier, one or more features associated with the globally unique mapping identifier;

mapping, for each globally unique mapping identifier, the identified one or more features to the globally unique mapping identifier, thereby providing mapping data indicating mapping between a plurality of features and the plurality of globally unique mapping identifiers, wherein at least some features having different names but corresponding to a same gene, SNP, SNP pattern, portion of gene, region of a genome, or compound are mapped to a same globally unique mapping identifier;

storing the mapping data in an index set;

identifying, for each of a plurality of the categories in the taxonomy, contributing feature sets that contribute to scoring the category under consideration by identifying all feature sets among the provided feature sets that are associated with the category under consideration and its child categories in the taxonomy;

obtaining, based on the feature ranks of features in the contributing feature sets that can be mapped to a same globally unique mapping identifier according to the mapping data in the index set, feature set-feature set correlation scores between the contributing feature sets and a plurality of other feature sets in the knowledge base, and feature set-feature group correlation scores between the contributing feature sets and a plurality of feature groups in the knowledge base;

calculating overall scores indicating correlation between the category under consideration and each of a plurality of features, feature sets and feature groups in the knowledge base based on the feature set-feature set correlation scores, feature set-feature group correlation scores, and feature ranks;

storing the overall scores on the one or more storage devices;

for each of a plurality of categories in the taxonomy, receiving from the one or more storage devices feature-set correlation scores between the contributing feature sets and a feature set obtained from a person; and combining the feature-set correlation scores to obtain a category-feature set score indicating the relevance of the category under consideration to the feature set obtained from the person; and determining whether the person is likely to have a disease or a phenotype by comparing the category-feature set score to a criterion.

19. The computer-implemented method of claim 18, further comprising generating a feature set from raw data associated with an experiment.

20. The computer-implemented method of claim 18, wherein the features of a plurality of feature sets are units of genetic information and the associated statistics indicate expression profiles.

21. The computer-implemented method of claim 18, further comprising identifying categories relevant to a feature, feature set or feature group based on the stored scores and displaying to a user the identified relevant categories.

* * * * *